US007754222B2

(12) United States Patent
Welch et al.

(10) Patent No.: US 7,754,222 B2
(45) Date of Patent: *Jul. 13, 2010

(54) SAFE MUTANT VIRAL VACCINES

(75) Inventors: Siao-Kun Wan Welch, Kalamazoo, MI (US); Jay Gregory Calvert, Otsego, MI (US); Michael K O'Hara, Kalamazoo, MI (US); Xuemei Cao, Scituate, MA (US)

(73) Assignee: Pharmacia & Upjohn Company, LLC, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/098,015

(22) Filed: Apr. 4, 2008

(65) Prior Publication Data
US 2008/0286302 A1    Nov. 20, 2008

Related U.S. Application Data

(63) Continuation of application No. 10/893,712, filed on Jul. 16, 2004, now Pat. No. 7,361,357.

(60) Provisional application No. 60/490,834, filed on Jul. 29, 2003.

(51) Int. Cl.
*A61K 39/12* (2006.01)
*A61K 39/295* (2006.01)

(52) U.S. Cl. .................................................. 424/218.1
(58) Field of Classification Search ....................... None
See application file for complete search history.

(56) References Cited

U.S. PATENT DOCUMENTS

| 6,001,613 | A | 12/1999 | Donis et al. |
| 7,361,357 | B2 | 4/2008 | Welch et al. |
| 2004/0081666 | A1 | 4/2004 | Dominowski |
| 2007/0172877 | A1* | 7/2007 | Ellsworth et al. ............... 435/6 |

FOREIGN PATENT DOCUMENTS

| WO | 2004/017990 | 3/2004 |
| WO | 2004/093904 | 11/2004 |

OTHER PUBLICATIONS

O.M. Radostits et al. Veterinary Medicine: a Textbook of the Diseases of Cattle, Sheep, Pigs, Goats, and Horses. 9th edition (2000). Publisher, W.B. Saunders. p. 1101.*
Platt et al (Veterinary Immunology and Immunopathology 122:8-15, 2008).*
Becher et al., "Cytopathogenicity of Border Disease Virus Is Correlated with Integration of Cellular Sequences into the Viral Genome", Journal of Virology, 70(5):2992-2998, 1996.
Becher et al., "Ribosomal S27a Coding Sequences Upstream of Ubiquitin Coding Sequences in the Genome of a Pestivirus", Journal of Virology, 72(11):8697-8704, 1998.
Endsley et al., "Maternal antibody blocks humoral/but not T cell responses to BVDV", Biologicals, 31:123-125, 2003.
Endsley et al., "Bovine Viral Diarrhea Virus Type 1- and Type 2-Specific Bovine T Lymphocyte-Subset Responses Following Modified-Live Virus Vaccination", Veterinary Therapeutics, 3(4):364-372, 2002.
Fulton et al., "Antibody responses by cattle after vaccination with commercial viral vaccines containing bovine herpesvirus-1, bovine viral diarrhea virus, parainfluenza-3 virus, and bovine respiratory syncytial virus immunogens and subsequent revaccination at day 140", Vaccine, 13(8):725-733, 1995.
Mendez et al., "Infectious Bovine Viral Diarrhea Virus (Strain NADL) RNA from Stable cDNA Clones: a Cellular Insert Determines NS3 Production and Viral Cytopathogenicity", Journal of Virology, 72(6):4737-4745, 1998.
Scherer et al., "Experimental infection of pregnant ewes with bovine viral diarrhea virus type-2 (BVDV-2): effects on the pregnancy and fetus", Veterinary Microbiology, 79:285-299, 2001.
Willson et al., "T

OTHER PUBLICATIONS

Ridpath and Bolin, "Delayed Onset Postvaccinal Mucosal Disease as a Result of Genetic Recombination between Genotype 1 and Genotype 2 BVDV", Virology, 212:259-262, 1995.

Ridpath and Neill, "Detection and Characterization of Genetic Recombination in Cytopathic Type 2 Bovine Viral Diarrhea Viruses", Journal of Virology, 74(18):8771-8774, 2000.

Vilcek et al., "Cellular insertions in the NS2-3 genome region of cytopathic bovine viral diarrhoea virus (BVDV) isolates", Veterinary Microbiology, 77:129-136, 2000.

Wang et al., "Evolutionary implications of genetic variations in the S1 gene of infectious bronchitis virus", Virus Research, 34:327-338, 1994.

Worobey and Holmes, "Evolutionary aspects of recombination in RNA viruses", Journal of General Virology, 80:2535-2543, 1999.

Worobey et al., "Widespread intra-serotype recombination in natural populations of dengue virus", Proc. Natl. Acad. Sci. USA, 96:7352-7357, 1999.

Ellsworth et al., "Efficacy of Bovi-Shield(R) GOLD 5 vaccine against bovine viral diarrhea virus type 2 respiratory challenge", Pfizer Animal Health Technical Bulletin, 2003, pp. 1-8.

Venugopal and Gould, "Towards a new generation of flavivirus vaccines", Butterworth Scientific, Guildford, GB, 12(11):966-975, 1994.

Widjojoatmodjo et al., "Classical Swine Fever Virus Ems Deletion Mutants: trans-Complementation and Potential Use as Nontransmissible, Modified, Live-Attenuated Marker Vaccines", Journal of Virology, 74(7):2973-2980, 2000.

PCT International Search Report, PCT/US2004/024011, mailed Oct. 4, 2005.

* cited by examiner

SAFE MUTANT VIRAL VACCINES

CROSS REFERENCE TO RELATED APPLICATION

This application is a continuation of U.S. patent application Ser. No. 10/893,712, filed Jul. 16, 2004, now allowed, which claims the benefit of U.S. Provisional Patent Application No. 60/490,834, filed Jul. 29, 2003, the entire disclosures of which are incorporated herein by reference.

FIELD OF THE INVENTION

The present invention relates generally to vaccines suitable for administration to animals against viral infections. More specifically, the present invention relates to safe vaccines and methods of preparing such vaccines. The vaccines of the present invention contain at least two live mutant viruses of the same family or nucleic acid molecules encoding such viruses, wherein each of the viruses or the encoding nucleic acids contains a mutation that confers a desirable phenotype and the mutations in the viruses reside in the same genomic site such that the mutant viruses cannot recombine with each other to eliminate the mutations.

BACKGROUND OF THE INVENTION

The virus family Flaviviridae consists of the genera Pestivirus, Flavivirus and Hepacivirus. The genus Pestivirus is represented by the species Bovine viral diarrhea virus 1 (BVDV-1), BVDV-2, classical swine fever virus, and Border disease virus. The virions of the family members encapsulate positive-strand RNA genomes of about 9.5 to 12.3 kb. The genomic RNAs contain contiguous long open reading frames (ORFs), which are translated into polyproteins that are processed by cellular and viral proteases to give rise to the mature viral proteins. For members of Pestivirus, the ORF encodes a polyprotein of about 3900 amino acids, which is cotranslationally and posttranslationally processed to the following mature viral proteins (from 5' to 3'): $N^{pro}$, C, $E^{rns}$, E1, E2, NS2-3, NS4A, NS4B, NS5A, and NS5B.

Two biotypes are found among some members of Pestivirus based on their effect on tissue culture cells, namely cytopathogenic (cytopathic or cp) and noncytopathogenic (noncytopathic or ncp). Genome analyses revealed insertions of cellular sequences, sometimes accompanied by duplication of viral sequences, genomic rearrangements, and/or deletions of viral sequences in the genomes of cp pestiviruses, but not in the RNAs of the corresponding ncp pestiviruses. This suggests that cp pestiviruses are evolved from ncp pestiviruses by RNA recombination.

BVDV is a widely distributed pathogen of cattle. BVDV-1 usually produces only mild diarrhea in immunocompetent animals, whereas BVDV-2 can produce thrombocytopenia, hemorrhages and acute fatal disease. BVDV is capable of crossing the placenta of pregnant cattle and may result in the birth of persistently infected (PI) calves (Malmquist, *J. Am. Vet. Med. Assoc.* 152:763-768 (1968); Ross, et al., *J. Am. Vet. Med. Assoc.* 188:618-619 (1986)). Viremic calves are immunotolerant to the virus and persistently viremic for the rest of their lives. They provide a source for outbreaks of mucosal disease (Liess, et al., *Dtsch. Tieraerztl. Wschr.* 81:481-487 (1974)) and are highly predisposed to infection with microorganisms causing diseases such as pneumonia or enteric disease (Barber, et al., *Vet. Rec.* 117:459-464 (1985)). Viruses of either genotype may exist as one of the two biotypes, cp or ncp. The cp phenotype correlates with the expression of NS3, since cells infected with either cp or ncp BVDV both express NS2-3, whereas NS3 is detected only after infection with cp BVDV. NS3 is colinear to the C-terminal part of NS2-3. The expression of NS3 appears to be a result of genomic alterations observed for cp BVDV.

Presently available viral vaccines include killed or attenuated live viral vaccines, live-vectored vaccines, subunit vaccines, and DNA or RNA vaccines. See Roth et al., "New Technology For Improved Vaccine Safety And Efficacy", *Veterinary Clinics North America: Food Animal Practice* 17(3): 585-597 (2001). Attenuation of viruses can be achieved by UV irradiation, chemical treatment, or high serial passage in vitro. The number, position and nature of mutations induced by these methods are unknown absent genomic sequence analyses. Attenuation can also be achieved by making defined genetic alterations, for example, specific deletion of viral sequences known to confer virulence, or insertion of sequences into the viral genome. One concern with respect to the use of attenuated live viral vaccines is that attenuated mutant viruses have the potential to recombine in vivo to eliminate the attenuating mutation(s) thereby restoring virulence. For example, in the presence of a virulent (wild type) field strain, attenuated viruses having deletions in the viral genome have the potential to recombine with the virulent strain to restore the deleted sequence. See, e.g., Roth et al., supra. Cytopathic pestiviruses having cellular insertions have also been observed to give rise to noncytopathic viruses in cell culture by deletion of the cellular sequences, possibly through RNA recombination. See, e.g., Baroth et al., "Insertion of cellular NEDD8 coding sequences in a pestivirus", *Virology.* 278(2): 456-66, (2000), and Becher et al., "RNA recombination between persisting pestivirus and a vaccine strain: generation of cytopathogenic virus and induction of lethal disease", *Journal of Virology* 75(14): 6256-64 (2001). Where it is desired to include two attenuated mutant viruses from the same species, genus or family in a vaccine composition, there is a concern that the two viruses may recombine in the vaccinated animal thereby eliminating the attenuating mutations. See, e.g., Glazenburg et al., "Genetic recombination of pseudorabies virus: evidence that homologous recombination between insert sequences is less frequent than between autologous sequences", *Archives of Virology,* 140(4): 671-85 (1995).

There remains a need to develop safe and effective vaccines that protect animals against viral infections.

SUMMARY OF THE INVENTION

The present invention provides safe vaccines which contain at least two live mutant viruses of the same family or nucleic acid molecules encoding such viruses, wherein each virus or the encoding nucleic acid contains a mutation that confers a desirable phenotype, and the mutations in the viruses reside in the same genomic site such that the mutant viruses cannot recombine with each other to eliminate the mutations.

The present invention also provides a method of preparing a safe viral vaccine by selecting or constructing two or more live mutant viruses of the same family, genus or species, wherein each virus contains a mutation that confers a desirable phenotype, and the mutations in the viruses reside in the same genomic site such that the mutant viruses can not undergo homologous recombination to eliminate the mutations.

The present invention further provides a method of protecting an animal against viral infections by administering to the animal a vaccine composition of the present invention.

DETAILED DESCRIPTION OF THE INVENTION

Figure 1:
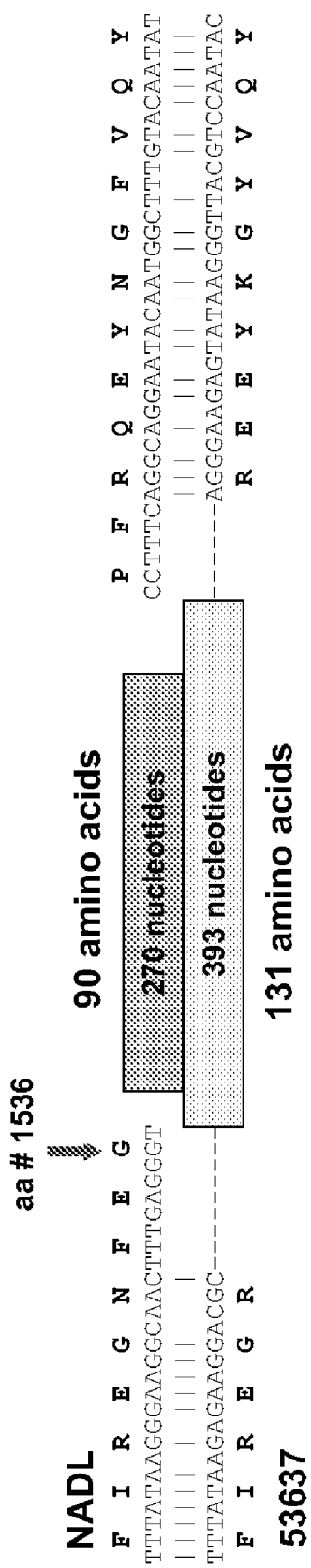
FIG. 1. Alignment of the cellular insertions and flanking viral sequences from the NS2-3 regions of BVDV-1 strain NADL (SEQ ID NOs: 11 to 14 and BVDV-2 strain 53637 (SEQ ID NOs: 15 to 18).

It has been uniquely recognized in accordance with the present invention that live mutant viruses of the same family, which contain mutations at the same genomic site of the viruses, cannot recombine with one another to eliminate the mutations.

Accordingly, in one embodiment, the present invention provides safe vaccine compositions containing at least two, i.e., two or more, live mutant viruses of the same family, or nucleic acid molecules encoding such viruses, wherein the mutations in the viruses reside in the same genomic site such that the mutant viruses cannot recombine with each other to eliminate the mutations.

In another embodiment, the present invention provides a method of preparing a safe viral vaccine, as described hereinabove. Specifically, a safe vaccine is prepared by selecting or constructing two or more live mutant viruses of the same family, genus or species, wherein each virus contains a mutation that confers a desirable phenotype (for example attenuation of virulence, alteration of cellular tropism or biotype, alteration of species tropism, or expression of a foreign gene cassette), and the mutations in the viruses reside in the same genomic site such that the mutant viruses can not undergo homologous recombination with each other to eliminate the mutations.

The term "vaccine" or "vaccine composition" refers to a composition containing live mutant viruses which, upon inoculation into an animal, induces a complete or partial immunity to the pathogenic version of the viruses, or alleviates the symptoms of diseases caused by the pathogenic versions of the viruses. The protective effects of a vaccine composition against a virus are normally achieved by inducing in the subject an immune response, either a cell-mediated or a humoral immune response, or a combination of both. Generally speaking, abolished or reduced incidences of viral infection, amelioration of the symptoms, or accelerated elimination of the viruses from the infected subjects, are indicative of the protective effects of the vaccine composition.

By "animal" is meant to include birds, for example, chickens, turkeys, domestic waterfowl, and any mammal, for example, cattle, sheep, swine, goats, dogs, cats, and horses.

The term "viruses", "viral isolates" or "viral strains" as used herein refer to viral particles or virions that contain viral genomic DNA or RNA, associated proteins, and other chemical constituents (such as lipids).

By "nucleic acid molecule encoding a virus" or "nucleic acid molecule of a virus" is meant the genomic nucleic acid molecule of the virus, either in the form of RNA or DNA.

By "mutation" is meant to include deletion, insertion or substitution of one or more nucleotides, or a combination thereof. In accordance with the present invention, the mutation preferably confers a desirable phenotype, for example attenuation of virulence, alteration of cellular tropism or biotype, alteration of species tropism, or expression of a foreign gene cassette. Especially preferred mutations are mutations that confer attenuated virulence.

By "attenuation" is meant that the virus has lost some or all of its ability to proliferate and/or cause disease in an animal infected with the virus. For example, an attenuated virus can be a virus that is unable to replicate at all or is limited to one or a few rounds of replication, or restricted in cell or tissue tropism, when present in an animal in which a wild type pathogenic version of the attenuated virus can replicate.

An attenuated virus may have one or more mutations in a gene or genes that are involved in pathogenicity of the virus. Such mutations are also referred to herein as "attenuating mutation(s)". An attenuated virus can be produced from the wild type, pathogenic virus by UV irradiation, chemical treatment, or high serial passage of the wild type, pathogenic virus in vitro. Alternatively, an attenuated virus can be produced from the wild type, pathogenic virus by making specific deletion of viral sequences known to confer virulence, insertion of sequences into the viral genome, or making one or more point mutations in the viral genome. An attenuated virus can be a viral isolate obtained from an animal, which isolate is derived from the wild type, pathogenic version of the virus through events other than artificial means, e.g., events that have occurred in a host animal such as recombination.

The two or more live mutant viruses present in the vaccine compositions of the present invention contain mutations that reside in the same genomic site. By "same genomic site" is meant that when the genomic nucleotide sequences of the viruses are aligned, the mutations in the viral genomes overlap with one another such that there is no opportunity for homologous recombination between and among the viral genomes to eliminate the mutations. In other words, when the genomic nucleotide sequences of the viruses are aligned, there is at least one contiguous portion of the aligned sequences where the sequences in the aligned viral genomes are mutant sequences. There are a number of computer programs that compare and align nucleic acid sequences which one skilled in the art may use. The sequences are aligned for optimal comparison purposes (e.g., gaps can be introduced in a nucleic acid sequence for optimal alignment with a second nucleic acid sequence). For example, the NBLAST and XBLAST programs as described in Altschul, et al., 1990, *J. Mol. Bid.* 215:403-410, the Gapped BLAST program as described in Altschul et al., 1997, *Nucleic Acids Res.* 25:3389-3402, and the PSI-Blast program as described in Altschul et al., 1997, supra. When utilizing BLAST, Gapped BLAST, and PSI-Blast programs, the default parameters of the respective programs (e.g., XBLAST and NBLAST) can be used (see the United States government web site from the National Center for Biotechnology Information, US National Library of Medicine, National Institutes of Health).

Generally speaking, the concept of the present invention, i.e., including in the same vaccine composition two or more live mutant viruses of the same family having mutations at the same genomic site, applies to mutant viruses from any family where the viral genomes have sufficient sequence identity to permit homologous recombination. It has been shown that a nucleotide identity as short as 15 nucleotides can lead to efficient homologous recombination (Nagy and Bujarski, *J. Virol.* 69:131-140, 1995).

The present invention applies especially to viruses of the Flaviviridae family. The Flaviviridae family consists of the genera Pestivirus, Flavivirus and Hepacivirus. The virions of the Flaviviridae family members encapsulate positive-strand RNA genomes of about 9.5 to 12.3 kb. The genomic RNAs containing contiguous long open reading frames, which are translated into polyproteins that are processed by cellular and viral proteases to give rise to the mature viral proteins.

Preferably, the mutant viruses of the vaccine composition of the present invention are from the same genus, either the same or different species.

In a preferred embodiment, the vaccine composition of the present invention contains two or more live mutant viruses from the Pestivirus genus. The genus Pestivirus is represented by the species Bovine Viral Diarrhea Virus Type 1 (BVDV-1), Bovine Viral Diarrhea Virus Type 2 (BVDV-2), classical swine fever virus, and Border disease virus. The ORF encodes a polyprotein of about 3900 amino acids, which is co-translationally and post-translationally processed to the following mature viral proteins (from 5' to 3'): $N^{pro}$, C, $E^{ms}$, E1, E2, NS2-3, NS4A, NS4B, NS5A, and NS5B.

Ordinarily, BVDV has a genome in the form of RNA. RNA can be reverse-transcribed into DNA for use in cloning. Thus, references made herein to nucleic acid and BVD viral sequences encompass both viral RNA sequences and DNA sequences derived from the viral RNA sequences. For convenience, genomic sequences of BVDV as depicted in the SEQUENCE LISTING hereinbelow only refer to the DNA sequences. The corresponding RNA sequence for each is readily apparent to those of skill in the art.

In a more preferred embodiment, the vaccine composition of the present invention contains a cytopathic BVDV-1 and a cytopathic BVDV-2, wherein the mutations in both viruses associated with the cytopathic biotype reside in the same genomic site such that the two mutant viruses cannot recombine to eliminate the mutations.

BVDV-1 and BVDV-2 represent two closely related genotypes of BVDV. The nucleotide sequences of the two viruses share about 70% identity over the entire genome, and slightly higher percent identity within the NS2-3 region. It is believed that the percent identity between the viral genomes of BVDV-1 and BVDV-2, at least in the NS2-3 region, is sufficient to permit homologous recombination.

BVDV-1 usually produce only mild diarrhea in animals, whereas BVDV-2 are viruses with high virulence which can produce thrombocytopenia, hemorrhages and acute fatal disease (Corapi et al., *J. Virol.* 63: 3934-3943; Bolin et al., *Am. J. Vet. Res.* 53: 2157-2163; Pellerin et al., *Virology* 203: 260-268, 1994; Ridpath et al., *Virology* 205: 66-74, 1994; Carman et al., *J. Vet. Diagn. Invest.* 10: 27-35, 1998). The two types of viruses have distinct antigenicity determined by a panel of MAbs and by cross-neutralization using virus-specific antisera raised in animals (Corapi et al., *Am. J. Vet. Res.* 51: 1388-1394, 1990). Viruses of either genotype may exist as one of the two biotypes, cytopathogenic (cytopathic or cp) or noncytopathogenic (noncytopathic or ncp). Cp viruses induce cytopathic effects (e.g., cell lysis) on cultured cells, while noncytopathic viruses do not.

It is desirable to prepare vaccines that provide protection against both BVDV-1 and BVDV-2. However, because of the high degree of sequence identity between the two viruses, there is a possibility that a live cytopathic BVDV-1 and a live cytopathic BVDV-2 included in the same vaccine composition, could recombine with each other in the vaccinated animal to yield noncytopathic viruses. Recombination between BVDV-1 and BVDV-2 has been documented. See, e.g., Ridpath et al., *Virology* 212: 259-262 (1995). Infection of the fetus in pregnant cattle with ncp viruses before immunocompetence develops can result in the fetus remaining viremic through the period of gestation and the subsequent birth of a calf that remains persistently viremic. Such a calf can die of mucosal disease upon superinfection with a cp BVDV. Accordingly, the vaccine compositions provided by the present invention, which contain live cp BVDV-1 and live cp BVDV-2 having mutations at the same genomic site, are especially desirable for protecting animals against both BVDV-1 and BVDV-2.

In one embodiment, BVDV cp isolates obtained from animals can be used in the vaccine composition of the present invention. Cp isolates of both BVDV-1 and BVDV-2 have been reported and are available to those skilled in the art, e.g., BVDV-1 NADL (ATCC# VR1422 or VR-534), BVDV-2 53637 strain (deposited with the ATCC as PTA-4859), and type 2 field isolates such as those described by Ridpath and Neill, *J. Virol* 74:8771-8774, (2000). Cp isolates reported so far typically contain an insertion of a heterologous sequence, e.g., an ubiquitin coding sequence (Genbank accession number M96687 or De Moerlooze et al., *J. Gen. Virol.* 74:1433-1438, (1993)), a bovine NEDD8 coding sequence (Baroth et al., supra), or a *Bos taurus* DnaJ1 coding sequence (as described in the Examples hereinbelow), among others.

In another embodiment, a cp BVDV is generated by making defined alterations in the BVDV genome, e.g., by deleting specific viral sequences, inserting sequences into a specific viral genomic site, or making one or more substitutions, or combinations thereof.

Where a cp BVDV is generated by inserting a heterologous (i.e., foreign to the virus) sequence into a specific genomic site, the nature of the sequence to be inserted is generally not critical to the present invention. In addition, the insertion is not limited to any particular site so long as the insertion results in an attenuated phenotype. As heterologous sequences in cp isolates are often found in the NS2-3 region, the NS2-3 region, especially the part surrounding the putative NS2-3 cleavage site which corresponds to, e.g., amino acid residues # 1679 to #1680 of the BVDV-1 NADL strain (the numbering is based on the published genomic sequence Genbank accession No. M31182, SEQ ID NO: 4), is a preferred location for insertions.

An cp BVDV-1 can be generated by making a defined genomic alteration that mimics the mutation identified in a cp BVDV-2 isolate obtained from an animal, such that these viruses have mutations associated with the cp biotype in the same genomic site. Similarly, a cp BVDV-2 can be generated by way of making a defined genomic alteration that mimics the mutation identified in a cp BVDV-1 isolate obtained from an animal.

In a preferred embodiment, the vaccine composition of the present invention contains NADL (a cp BVDV-1 isolate), and BVDV-2 53637 (a cp BVDV-2 isolate), where the two cp isolates each contain a mutation at the same genomic site which results in the cytopathic biotype. The genomic sequence of the BVDV-1 NADL strain is set forth in SEQ ID NO: 4, and the BVDV-2 53637 strain was deposited with the ATCC as PTA-4859. Both isolates contain an insertion in the NS2-3 region. The attenuated cp BVDV-1 contains an insertion of a *Bos taurus* DnaJ1 coding sequence 3' of the thymidine at nucleotide position # 4993 (NADL sequence numbering), which is the third nucleotide of the codon encoding the glycine residue at amino acid position 1536. The attenuated cp BVDV-2 contains an insertion of a *Bos taurus* DnaJ1 coding sequence at the same genomic site.

According to the present invention, the cp BVDV isolates employed in the present vaccine composition have been attenuated and are therefore nonpathogenic. Methods of attenuation are known to those skilled in the art and are also described hereinbelow.

In another embodiment, the vaccine composition of the present invention contains an attenuated BVDV-1 and an attenuated BVDV-2, wherein the attenuating mutations in both viruses reside in the same genomic site such that the two mutant viruses cannot recombine to eliminate the attenuating mutations.

An attenuated BVDV is generated by UV irradiation, chemical treatment, or high serial passage of the pathogenic version of the viruse in vitro. Sequence analysis can be conducted in order to determine the nature and genomic location of mutations generated by these methods. The mutation can be in the form of a deletion, insertion or substitution of one or more nucleotides, or a combination thereof. Alternatively, an attenuated BVDV is generated by making defined alterations in the BVDV genome, e.g., by deleting specific viral sequences, inserting sequences into a specific viral genomic site, or making one or more substitutions, or combinations thereof.

As described above, the live mutant viruses for use in the vaccine composition of the present invention can be from the same family, genus or species, where the viral genomes have sufficient sequence identity to permit homologous recombination. Additional examples of combinations of viruses appropriate for use in the vaccine composition of the present invention include, but are not limited to, combinations of different types of poliovirus, combinations of multiple live mutant strains of infectious bronchitis virus, combinations of multiple live mutant strains of Newcastle disease virus, combinations of Canine adenovirus-1 and canine adenovirus-2, combinations of equine herpesvirus-1 and equine herpesvirus-4, combinations of multiple live mutant strains of influenza virus, combinations of multiple live attenuated strains of Feline calicivirus, combinations of multiple serotypes of Rotavirus, combinations of multiple serotypes of Rhinovirus, combinations of multiple serotypes of Foot and Mouth Disease virus, combinations of the European and North American genotypes of Porcine reproductive and respiratory syndrome virus, combinations of standard and variant strains of infectious bursal disease virus.

In accordance with the present invention, although viral particles are the preferred form for use in the vaccines, nucleic acid molecules encoding mutant viruses of the same family, genus or species, can be used directly in vaccines as well. The DNA or RNA molecule can be present in a "naked" form or it can be combined with an agent which facilitates cellular uptake (e.g., liposomes or cationic lipids). Vaccines and vaccination procedures that utilize nucleic acids (DNA or mRNA) have been well described in the art, e.g., U.S. Pat. No. 5,703,055, U.S. Pat. No. 5,580,859, U.S. Pat. No. 5,589,466, International Patent Publication WO 98/35562, and by Ramsay et al., 1997, *Immunol. Cell Biol.* 75:360-363; Davis, 1997, *Cur. Opinion Biotech.* 8: 635-640; Manickan et al., 1997, *Critical Rev. Immunol.* 17: 139-154; Robinson, 1997, *Vaccine* 15(8): 785-787; Robinson et al., 1996, *AIDS Res. Hum. Retr.* 12(5): 455-457; Lai and Bennett, 1998, *Critical Rev. Immunol.* 18:449-484; and Vogel and Sarver, 1995, *Clin. Microbiol. Rev.* 8(3): 406-410, all of which are incorporated herein by reference.

In addition to two or more live mutant viruses from the same family, genus or species, the vaccine compositions can include other antigenic component. Other antigenic components appropriate for use in accordance with the present invention include, but are not limited to, antigens prepared from pathogenic bacteria such as *Mycoplasma hyopneumonia, Haemophilus somnus, Haemophilus parasuis, Bordetella bronchiseptica, Bacillus anthracis, Actinobacillus pleuropneumonie, Pasteurella multocida, Mannhemia haemolytica, Mycoplasma bovis, Mycoplasma galanacieum, Mycoplasma gallisepticum, Mycobacterium bovis, Mycobacterium paratuberculosis, Clostridial* spp., *Streptococcus uberis, Streptococcus suis, Staphylococcus aureus, Erysipelothrix rhusopathiae, Campylobacter* spp., *Fusobacterium necrophorum, Escherichia coli, Lawsonia intracellularis, Listeria monocytogenes, Rickettsia rickettsii, Borrelia* spp., *Ehrlichia* spp., *Chlamydia* spp., *Brucella* spp., *Vibrio* spp., *Salmonella enterica serovars, Leptospira* spp.; pathogenic fungi such as *Candida*; protozoa such as *Cryptosporidium parvum, Neospora canium, Toxoplasma gondii, Eimeria* spp., *Babesia* spp., *Giardia* spp.; helminths such as *Ostertagia, Cooperia, Haemonchus, Fasciola*; either in the form of an inactivated whole or partial cell preparation, or in the form of antigenic molecules obtained by genetic engineering techniques or chemical synthesis. Additional antigens include pathogenic viruses such as Marek's disease virus, infectious bursal disease virus, Newcastle's disease virus, chicken anemia virus, fowlpox virus, avian leukosis virus, infectious laryngotracheitis virus, reticuloendothelial virus, canine parvovirus, canine distemper virus, canine herpesvirus, canine coronavirus, canine parainfluenza-5, feline panleukopenia virus, feline herpes virus, feline calicivirus, feline immunodeficiency virus, feline infectious peritonitis virus, equine herpesvirus, equine arteritis virus, equine infectious anemia virus, Eastern equine encephalitis virus, Western equine encephalitis virus, Venezuelan equine encephalitis virus, West Nile virus, transmissible gastroenteritis virus, bovine coronavirus, Bovine herpesviruses-1,3,6, Bovine parainfluenza virus, Bovine respiratory syncytial virus, bovine leukosis virus, rinderpest virus, foot and mouth disease virus, rabies virus, African swine fever virus, Porcine parvovirus, PRRS virus, Porcine circovirus, influenza virus, swine vesicular disease virus, Techen fever virus, Pseudorabies virus, either in the form of modified live (attenuated) viral preparation, an inactivated whole or partial virus preparation, or in the form of antigenic molecules obtained by genetic engineering techniques or chemical synthesis. When additional attenuated live viruses are used, such additional viruses should preferably be from a family different from that of the two principal attenuated viruses, as described above.

In a preferred embodiment, the present invention provides a vaccine composition which contains an attenuated cp BVDV-1 derived from the BVDV-1 NADL strain, an attenuated cp BVDV-2 derived from the BVDV-2 53637 strain, where the two cp isolates each contain a mutation associated with the cp biotype at the same genomic site, and at least one (i.e., one or more) of the following antigenic component, either in inactivated or modified live form: bovine herpesvirus-1, bovine respiratory syncytial virus, parainfluenza virus-3, *Campylobacter fetus, Leptospira canicola, Leptospira grippotyphosa, Leptospira hardjo, Leptospira icterohaemorrhagiae, Leptospira pomona*, or *Mannhemia haemolytica*.

In addition, the vaccine compositions of the present invention can include one or more veterinarily-acceptable carriers. As used herein, "a veterinarily-acceptable carrier" includes any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others. Stabilizers include albumin, among others. The vaccine compositions can further include one or more other immunomodulatory agents such as, e.g., interleukins, interferons, or other cytokines Adjuvants suitable for use in the vaccine compositions include, but are not limited to, the RIBI adjuvant system (Ribi inc.), alum, aluminum hydroxide gel, oil-in water emulsions, water-in-oil emulsions such as, e.g., Freund's complete and incomplete adjuvants, Block co polymer (CytRx, Atlanta Ga.), SAF-M (Chiron, Emeryville Calif.), AMPHIGEN® adjuvant, saponin, Quil A, cholesterol, QS-21 (Cambridge Biotech Inc., Cambridge Mass.), or other saponin fractions, monophosphoryl lipid A, Avridine lipid-amine adjuvant, heat-labile enterotoxin from *E. coli* (recombinant or otherwise), cholera toxin, or muramyl dipeptide, among many others.

Typically, a live mutant virus is present in a vaccine at an amount of about $1\times10^6$ and about $1\times10^8$ virus particles per dose, with a veterinarily acceptable carrier, in a volume of between about 0.5 and about 5 ml. The precise amount of a virus in a vaccine composition effective to provide a protective effect can be determined by a skilled veterinarian. Where the DNA or RNA molecule of the virus is used in the vaccine, the amount of the nucleic acids should generally be between about 0.1 µg/ml and about 5.0 mg/ml.

The vaccine compositions of the present invention can be made in various forms depending upon the route of administration. For example, the vaccine compositions can be made in the form of sterile aqueous solutions or dispersions suitable for injectable use, or made in lyophilized forms using freeze-drying techniques. Lyophilized compositions are typically maintained at about 4° C., and can be reconstituted in a stabilizing solution, e.g., saline or and HEPES, with or without adjuvant.

The vaccine compositions of the present invention can be administered to an animal for treating or preventing a disease caused by the pathogenic versions of the viruses in the vaccine compositions. Therefore, methods of vaccinating an animal against a disease caused by a virus are also provided by the present invention.

In practicing the present methods, a vaccine composition of the present invention is administered to an animal preferably via parenteral routes, although other routes of administration can be used as well, such as e.g., by oral, intranasal, intramuscular, intra-lymph node, intradermal, intraperitoneal, subcutaneous, rectal or vaginal administration, or by a combination of routes. Boosting regimens may be required and the dosage regimen can be adjusted to provide optimal vaccination.

The present invention is further illustrated by, but by no means limited to, the following examples.

Example I

Determination of the Position of the Cellular Insertion in BVDV2 Strain 53637

A portion of the sequence of the NS2-3 region from BVDV2-53637 was determined, in order to identify and map the location of any cellular insertions in the region. A 670 base RT-PCR product was amplified from viral RNA, using forward primer 53637U1 (5'-CGTCCACAGATGGTTTGGT-3'; SEQ ID NO: 1) and reverse primer 53637L (5'-GGCTAT-GTATTGGACGTAACCC-3'; SEQ ID NO: 2). The RT-PCR product was purified and submitted for sequence analysis (SEQ ID NO: 3). When aligned with BVDV1-NADL (Genbank accession number M31182, SEQ ID NO: 4), striking similarities were observed (FIG. 1). Both viruses contain an in-frame insertion derived from the *Bos taurus* DnaJ1 gene. In the case of NADL, the insertion is 90 amino acids (270 nucleotides) in length and is located between glycine-1536 and proline-1627 in the NADL polyprotein. These coordinates correspond to glycine-1536 and proline-1537 in non-cytopathic BVDV1 strains such as SD-1 (Genbank accession number AAA42860, SEQ ID NO: 6), indicating that the genome alteration in NADL is a simple insertion with no concomitant deletion or duplication of flanking viral sequences. Like BVDV1-NADL, there is an insertion of a portion of the *Bos taurus* DnaJ1 gene in BVDV2-53637. The cellular insertion is longer (131 amino acids, 393 nucleotides), being extended in both directions relative to the insertion in BVDV1-NADL. The location of the cellular insertion within the NS2-3 region is identical in the two viruses. Unlike BVDV1-NADL, the BVDV2-53637 insertion is accompanied by a deletion of 5 amino acids (15 nucleotides) of flanking viral sequences. Three amino acid residues are absent flanking the 5' end of the insertion, while two amino acids residues are absent flanking the 3' end of the insertion. Because the cellular insertions are at the same genome position in the two vaccine viruses, they cannot undergo homologous recombination to delete the insertion to generate a non-cytopathic chimeric virus.

Example II

Attempts to Detect Non-Cytopathic BVDV Viruses in Co-Passaged BVDV1-NADL/BVDV2-53637 Cultures In order to determine whether the two vaccine viruses are capable of recombining to generate detectable levels of non-cytopathic BVDV, the viruses were co-cultivated on susceptible cells and a sensitive hemi-nested RT-PCR assay was used to detect potential non-cytopathic viruses from among an excess of longer cytopathic products that still contain the cellular insert. To increase the probability of intertypic recombination in vitro, each virus was inoculated simultaneously onto confluent BK-6 cells in 6-well plates at a multiplicity of infection of 2-4 (12 replicates per experiment). After 2-3 days of co-cultivation the cells were frozen and thawed twice, and cell debris was removed by low speed centrifugation. The resulting supernatant fluid was then used as inoculum for the next passage. A total of seven serial passages were conducted in several studies. During the passages BVDV1-NADL grew more rapidly than BVDV2-53637, but the type II virus was still detectable after seven passages using nested RT-PCR. A sensitive hemi-nested RT-PCR assay was employed in an attempt to detect any non-cytopathic virus.

In first round RT-PCR, forward primers 53637U1 (SEQ ID NO: 1) or NADL4744 (5'-CGTGGCTTCTTGGTACGGG-3', SEQ ID NO: 7) were used in conjunction with reverse primers 53637L (SEQ ID NO: 2) or NADL5305 (5'-AGCG-GTATATTGTACAAAGCCA-3', SEQ ID NO: 8). All four combinations of forward and reverse primers were used in order to detect BVDV1, BVDV2, and intertypic recombinants. The expected size of RT-PCR product was 562 bp for cytopathic BVDV1-NADL and 670 bp for cytopathic BVDV2-53637. Non-cytopathic viruses, if present at detectable levels, would be expected to yield first round products of 292 bp (BVDV1-NADL) or 277 bp (BVDV2-53637). Intertypic recombinants should be similar in size to one of the parents, or of intermediate length, depending on the location of the recombination site. Non-cytopathic BVDVs were never detected following first round RT-PCR.

To increase the sensitivity of detecting non-cytopathic BVDV in the presence of a large excess of cytopathic BVDV, a restriction enzyme digestion step was included before the nested PCR to destroy the larger NS2-3 templates derived from the cytopathic viruses. A combination of MspI and DraI was selected based on the observation that they cut within the *Bos taurus* DnaJ1 insert but do not cut the flanking viral sequences. In second round (hemi-nested) PCR, forward primers 53637U2 (5'-TGCACGATCTGTGAAGGGAAA-GAA-3', SEQ ID NO: 9) or NADL4844 (5'-TGCACTGTAT- GTGAGGGCCGAGAG-3', SEQ ID NO: 10) were used in conjunction with the same two reverse primers 53637L or NADL5305. Appropriate primer combinations were used to attempt to detect intertypic recombinants as well as BVDV1 and BVDV2. The expected size of RT-PCR product is 462 bp for cytopathic BVDV1-NADL and 570 bp for cytopathic BVDV2-53637 (present at low levels due to incomplete digestion of the cytopathic BVDV RT-PCR products). Non-cytopathic viruses, if present at detectable levels, would be expected to yield second round products of 192 bp (BVDV1-NADL) or 177 bp (BVDV2-53637). Intertypic recombinants should be similar in size to one of the parents, or of intermediate length, depending on the location of the recombination site. Non-cytopathic BVDVs were never detected following second round PCR. In a few individual reactions, aberrant bands of various sizes were seen. All bands between 100 and 300 bp were considered to be potential non-cytopathic products and were submitted for DNA sequence analysis. In every case the aberrant band was the result of false priming during PCR. There was no evidence of non-cytopathic virus in any of the studies.

SEQ ID No Description
1 forward primer 53637U1
2 reverse primer 53637L
3 670 bp RT-PCR product from the NS2-3 region of BVDV2 strain 53637
4 genomic sequence of BVDV1-NADL (Genbank accession number M31182)
5 polyprotein sequence of BVDV1-NADL (Genbank accession number AAA42854)
6 polyprotein sequence of non-cytopathic BVDV1 strain SD-1 (Genbank accession number AAA42860)
7 forward primer NADL4744
8 reverse primer NADL5305
9 forward primer 53637U2
10 forward primer NADL4844

```
                                              SEQ NO: 1
cgtccacagatggtttggt

SEQ NO: 2
ggctatgtattggacgtaaccc

SEQ NO: 3
cgtccacagatggtttggtgaggaggaaatatatggggcacccaaggtga tcaccatcataaaagctagtaccctaagtaaaaacaggcactgcataatc tgcacgatctgtgaagggaaagaatggaacggagccaactgcccaaagtg tggaagacaaggaaagcccataacatgtggaatgacactcgcagactttg aggagaaacattacaaaaagatatttataagagaaggacgccaagaagca atgaatacgatgatgtgcagccgatgccagggaaagcataggaggtttga aacgaccgggaacctaagagtgccagatactgtgctgagtgtaataggc tgcatcctgctgaggaaggtgacttttgggcagagtcaagcatgttgggc ctcaaaatcacctactttgcgctgatggatggaaaggtgtatgatatcac agagtgggctggatgccagcgtgtgggaatctccccagatacccacagag tcccttgtcacatctcatttggttcacggatgccaggcaccagtgggcgg cagagagctactccagatgcccctcctgctgaccttcaggatttcttgag ccggatctttcaagtaccccaggccagatgtccagggaagagtataagg gttacgtccaatacatagcc
```

-continued
```
                                              SEQ ID: 4
gtatacgaga attagaaaag gcactcgtat acgtattggg caattaaaaa taataattag gcctagggaa caaatccctc tcagcgaagg ccgaaaagag gctagccatg cccttagtag gactagcata atgagggggg tagcaacagt ggtgagttcg ttggatggct taagccctga gtacagggta gtcgtcagtg gttcgacgcc ttggaataaa ggtctcgaga tgccacgtgg acgagggcat gcccaaagca catcttaacc tgagcggggg tcgcccaggt aaaagcagtt ttaaccgact gttacgaata cagcctgata gggtgctgca gaggcccact gtattgctac taaaaatctc tgctgtacat ggcacatgga gttgatcaca aatgaacttt tatacaaaac atacaaacaa aaacccgtcg gggtggagga acctgtttat gatcaggcag gtgatccctt atttggtgaa aggggagcag tccaccctca atcgacgcta aagctcccac acaagagagg ggaacgcgat gttccaacca acttggcatc cttaccaaaa agaggtgact gcaggtcggg taatagcaga ggacctgtga gcgggatcta cctgaagcca gggccactat tttaccagga ctataaaggt cccgtctatc acagggcccc gctggagctc tttgaggagg gatccatgtg tgaaacgact aaacggatag ggagagtaac tggaagtgac ggaaagctgt accacattta tgtgtgtata gatggatgta taataataaa aagtgccacg agaagttacc aaagggtgtt caggtgggtc cataataggc ttgactgccc tctatgggtc acaacttgct cagacacgaa agaagaggga gcaacaaaaa agaaaacaca gaaacccgac agactagaaa gggggaaaat gaaaatagtg cccaaagaat ctgaaaaaga cagcaaaact aaacctccgg atgctacaat agtggtggaa ggagtcaaat accaggtgag gaagaaggga aaaaccaaga gtaaaaacac tcaggacggc ttgtaccata acaaaaacaa acctcaggaa tcacgcaaga aactggaaaa agcattgttg gcgtgggcaa taatagctat agttttgttt caagttacaa tgggagaaaa cataacacag tggaacctac aagataatgg gacggaaggg atacaacggg caatgttcca aagggggtgtg aatagaagtt tacatggaat ctggccagag aaaatctgta ctggcgtccc ttcccatcta gccaccgata tagaactaaa aacaattcat ggtatgatgg atgcaagtga gaagaccaac tacacgtgtt gcagacttca acgccatgag tggaacaagc atggttggtg caactggtac aatattgaac cctggattct agtcatgaat agaacccaag ccaatctcac tgagggacaa ccaccaaggg agtgcgcagt cacttgtagg tatgataggg ctagtgactt
```

-continued

```
aaacgtggta acacaagcta gagatagccc cacacccttta
acaggttgca agaaaggaaa gaacttctcc tttgcaggca
tattgatgcg gggcccctgc aactttgaaa tagctgcaag
tgatgtatta ttcaaagaac atgaacgcat tagtatgttc
caggatacca ctctttacct tgttgacggg ttgaccaact
ccttagaagg tgccagacaa ggaaccgcta aactgacaac
ctggttaggc aagcagctcg ggatactagg aaaaaagttg
gaaaacaaga gtaagacgtg gtttggagca tacgctgctt
ccccttactg tgatgtcgat cgcaaaattg gctacatatg
gtatacaaaa aattgcaccc ctgcctgctt acccaagaac
acaaaaattg tcggccctgg gaaatttggc accaatgcag
aggacggcaa gatattacat gagatggggg gtcacttgtc
ggaggtacta ctactttctt tagtggtgct gtccgacttc
gcaccggaaa cagctagtgt aatgtaccta atcctacatt
tttccatccc acaaagtcac gttgatgtaa tggattgtga
taagacccag ttgaacctca cagtggagct gacaacagct
gaagtaatac cagggtcggt ctggaatcta ggcaaatatg
tatgtataag accaaattgg tggccttatg agacaactgt
agtgttggca tttgaagagg tgagccaggt ggtgaagtta
gtgttgaggg cactcagaga tttaacacgc atttggaacg
ctgcaacaac tactgctttt ttagtatgcc ttgttaagat
agtcaggggc cagatggtac agggcattct gtggctacta
ttgataacag gggtacaagg gcacttggat tgcaaacctg
aattctcgta tgccatagca aaggacgaaa gaattggtca
actgggggct gaaggcctta ccaccacttg aaggaatac
tcacctggaa tgaagctgga agacacaatg gtcattgctt
ggtgcgaaga tgggaagtta atgtacctcc aaagatgcac
gagagaaacc agatatctcg caatcttgca tacaagagcc
ttgccgacca gtgtggtatt caaaaaactc tttgatgggc
gaaagcaaga ggatgtagtc gaaatgaacg acaactttga
atttggactc tgcccatgtg atgccaaacc catagtaaga
gggaagttca atacaacgct gctgaacgga ccggccttcc
agatggtatg ccccatagga tggacaggga ctgtaagctg
tacgtcattc aatatggaca ccttagccac aactgtggta
cggacatata gaaggtctaa accattccct cataggcaag
gctgtatcac ccaaaagaat ctgggggagg atctccataa
ctgcatcctt ggaggaaatt ggacttgtgt gcctggagac
caactactat acaaaggggg ctctattgaa tcttgcaagt
ggtgtggcta tcaatttaaa gagagtgagg gactaccaca
ctaccccatt ggcaagtgta aattggagaa cgagactggt
```

-continued

```
tacaggctag tagacagtac ctccttgcaat agagaaggtg
tggccatagt accacaaggg acattaaagt gcaagatagg
aaaaacaact gtacaggtca tagctatgga taccaaactc
ggacctatgc cttgcagacc atatgaaatc atatcaagtg
agggcctgt agaaaagaca gcgtgtactt tcaactacac
taagacatta aaaataagt attttgagcc cagagacagc
tactttcagc aatacatgct aaaaggagag tatcaatact
ggttttgacct ggaggtgact gaccatcacc gggattactt
cgctgagtcc atattagtgg tggtagtagc cctcttgggt
ggcagatatg tactttggtt actggttaca tacatggtct
tatcagaaca gaaggcctta gggattcagt atggatcagg
ggaagtggtg atgatgggca acttgctaac ccataacaat
attgaagtgg tgacatactt cttgctgctg tacctactgc
tgagggagga gagcgtaaag aagtgggtct tactcttata
ccacatctta gtggtacacc caatcaaatc tgtaattgtg
atcctactga tgattgggga tgtggtaaag gccgattcag
ggggccaaga gtacttgggg aaaatagacc tctgttttac
aacagtagta ctaatcgtca taggtttaat catagctagg
cgtgacccaa ctatagtgcc actggtaaca ataatggcag
cactgagggt cactgaactg acccaccagc ctggagttga
catcgctgtg gcggtcatga ctataacccct actgatggtt
agctatgtga cagattattt tagatataaa aaatggttac
agtgcattct cagcctggta tctgcggtgt tcttgataag
aagcctaata tacctaggta gaatcgagat gccagaggta
actatcccaa actggagacc actaacttta atactattat
atttgatctc aacaacaatt gtaacgaggt ggaaggttga
cgtggctggc ctattgttgc aatgtgtgcc tatcttattg
ctggtcacaa ccttgtgggc cgacttctta accctaatac
tgatcctgcc tacctatgaa ttggttaaat tatactatct
gaaaactgtt aggactgata cagaaagaag ttggctaggg
gggatagact atacaagagt tgactccatc tacgacgttg
atgagagtgg agagggcgta tatcttttttc catcaaggca
gaaagcacag gggaattttt ctatactctt gccccttatc
aaagcaacac tgataagttg cgtcagcagt aaatggcagc
taatatacat gagttactta actttggact ttatgtacta
catgcacagg aaagttatag aagagatctc aggaggtacc
aacataatat ccaggttagt ggcagcactc atagagctga
actggtccat ggaagaagag gagagcaaag gcttaaagaa
gttttatcta ttgtctggaa ggttgagaaa cctaataata
aaacataagg taaggaatga gaccgtggct tcttggtacg
```

-continued

```
gggaggagga agtctacggt atgccaaaga tcatgactat
aatcaaggcc agtacactga gtaagagcag gcactgcata
atatgcactg tatgtgaggg ccgagagtgg aaaggtggca
cctgcccaaa atgtggacgc catgggaagc cgataacgtg
tgggatgtcg ctagcagatt ttgaagaaag acactataaa
agaatcttta aagggaagg caactttgag ggtatgtgca
gccgatgcca gggaaagcat aggaggtttg aaatggaccg
ggaacctaag agtgccagat actgtgctga gtgtaatagg
ctgcatcctg ctgaggaagg tgacttttgg gcagagtcga
gcatgttggg cctcaaaatc acctactttg cgctgatgga
tggaaaggtg tatgatatca cagagtgggc tggatgccag
cgtgtgggaa tctccccaga tacccacaga gtcccttgtc
acatctcatt tggttcacgg atgcctttca gcaggaata
caatggcttt gtacaatata ccgctagggg gcaactattt
ctgagaaact tgcccgtact ggcaactaaa gtaaaaatgc
tcatggtagg caaccttgga gaagaaattg gtaatctgga
acatcttggg tggatcctaa gggggcctgc cgtgtgtaag
aagatcacag agcacgaaaa atgccacatt aatatactgg
ataaactaac cgcatttttc gggatcatgc caagggggac
tacacccaga gccccggtga ggttccctac gagcttacta
aaagtgagga ggggtctgga gactgcctgg gcttacacac
accaaggcgg gataagttca gtcgaccatg taaccgccgg
aaaagatcta ctggtctgtg acagcatggg acgaactaga
gtggtttgcc aaagcaacaa caggttgacc gatgagacag
agtatgcgt caagactgac tcagggtgcc cagacggtgc
cagatgttat gtgttaaatc cagaggccgt taacatatca
ggatccaaag gggcagtcgt tcacctccaa aagacaggtg
gagaattcac gtgtgtcacc gcatcaggca caccggcttt
cttcgaccta aaaaacttga aaggatggtc aggcttgcct
atatttgaag cctccagcgg gagggtggtt ggcagagtca
aagtagggaa gaatgaagag tctaaaccta caaaaataat
gagtggaatc cagaccgtct caaaaaacag agcagacctg
accgagatgg tcaagaagat aaccagcatg aacaggggag
acttcaagca gattactttg gcaacagggg caggcaaaac
cacagaactc ccaaaagcag ttatagagga gataggaaga
cacaagagag tattagttct tataccatta agggcagcgg
cagagtcagt ctaccagtat atgagattga acacccaag
catctctttt aacctaagga taggggacat gaaagagggg
gacatggcaa ccgggataac ctatgcatca tacgggtact
tctgccaaat gcctcaacca aagctcagag ctgctatggt
agaatactca tacatattct tagatgaata ccattgtgcc
actcctgaac aactggcaat tatcgggaag atccacagat
tttcagagag tataagggtt gtcgccatga ctgccacgcc
agcagggtcg gtgaccacaa caggtcaaaa gcacccaata
gaggaattca tagcccccga ggtaatgaaa ggggaggatc
ttggtagtca gttccttgat atagcagggt taaaaatacc
agtggatgag atgaaaggca atatgttggt ttttgtacca
acgagaaaca tggcagtaga ggtagcaaag aagctaaaag
ctaagggcta taactctgga tactattaca gtggagagga
tccagccaat ctgagagttg tgacatcaca atcccctat
gtaatcgtgg ctacaaatgc tattgaatca ggagtgacac
taccagattt ggacacggtt atagacacgg ggttgaaatg
tgaaaagagg gtgagggtat catcaaagat acccttcatc
gtaacaggcc ttaagaggat ggccgtgact gtgggtgagc
aggcgcagcg tagggcaga gtaggtagag tgaaacccgg
gaggtattat aggagccagg aaacagcaac agggtcaaag
gactaccact atgacctctt gcaggcacaa agatacggga
ttgaggatgg aatcaacgtg acgaaatcct ttagggagat
gaattacgat tggagcctat acgaggagga cagcctacta
ataacccagc tggaaatact aaataatcta ctcatctcag
aagacttgcc agccgctgtt aagaacataa tggccaggac
tgatcaccca gagccaatcc aacttgcata caacagctat
gaagtccagg tcccggtcct attcccaaaa ataaggaatg
gagaagtcac agacacctac gaaaattact cgtttctaaa
tgccagaaag ttaggggagg atgtgcccgt gtatatctac
gctactgaag atgaggatct ggcagttgac ctcttagggc
tagactggcc tgatcctggg aaccagcagg tagtggagac
tggtaaagca ctgaagcaag tgaccgggtt gtcctcggct
gaaaatgccc tactagtggc tttatttggg tatgtgggtt
accaggctct ctcaaagagg catgtcccaa tgataacaga
catatatacc atcgaggacc agagactaga agacaccacc
cacctccagt atgcacccca cgccataaaa accgatggga
cagagactga actgaaagaa ctggcgtcgg tgacgtggaa
aaaaatcatg ggagccattt cagattatgc agctggggga
ctggagtttg ttaaatccca agcagaaaag ataaaaacag
ctcctttgtt taaagaaaac gcagaagccg caaaagggta
tgtccaaaaa ttcattgact cattaattga aaataaagaa
gaaataatca gatatggttt gtggggaaca cacacagcac
tatacaaaag catagctgca agactggggc atgaaacagc
gtttgccaca ctagtgttaa agtggctagc ttttggaggg
```

-continued

```
gaatcagtgt cagaccacgt caagcaggcg gcagttgatt
tagtggtcta ttatgtgatg aataagcctt ccttcccagg
tgactccgag acacagcaag aagggaggcg attcgtcgca
agcctgttca tctccgcact ggcaacctac acatacaaaa
cttggaatta ccacaatctc tctaaagtgg tggaaccagc
cctggcttac ctcccctatg ctaccagcgc attaaaaatg
ttcaccccaa cgcggctgga gagcgtggtg atactgagca
ccacgatata taaaacatac ctctctataa ggaaggggaa
gagtgatgga ttgctgggta cggggataag tgcagccatg
gaaatcctgt cacaaaaccc agtatcggta ggtatatctg
tgatgttggg ggtaggggca atcgctgcgc acaacgctat
tgagtccagt gaacagaaaa ggaccctact tatgaaggtg
tttgtaaaga acttcttgga tcaggctgca acagatgagc
tggtaaaaga aaacccagaa aaaattataa tggccttatt
tgaagcagtc cagacaattg gtaaccccct gagactaata
taccacctgt atggggttta ctacaaaggt tgggaggcca
aggaactatc tgagaggaca gcaggcagaa acttattcac
attgataatg tttgaagcct tcgagttatt agggatggac
tcacaaggga aaataaggaa cctgtccgga aattacattt
tggatttgat atacggccta cacaagcaaa tcaacagagg
gctgaagaaa atggtactgg ggtgggcccc tgcaccettt
agttgtgact ggacccctag tgacgagagg atcagattgc
caacagacaa ctatttgagg gtagaaacca ggtgcccatg
tggctatgag atgaaagctt tcaaaaatgt aggtggcaaa
cttaccaaag tggaggagag cgggccttte ctatgtagaa
acagacctgg tagggacca gtcaactaca gagtcaccaa
gtattacgat gacaacctca gagagataaa accagtagca
aagttggaag acaggtaga gcactactac aaaggggtca
cagcaaaaat tgactacagt aaaggaaaaa tgctcttggc
cactgacaag tgggaggtgg aacatggtgt cataaccagg
ttagctaaga gatatactgg ggtcgggtte aatggtgcat
acttaggtga cgagcccaat caccgtgctc tagtggagag
ggactgtgca actataacca aaaacacagt acagtttcta
aaaatgaaga aggggtgtgc gttcacctat gacctgacca
tctccaatct gaccaggctc atcgaactag tacacaggaa
caatcttgaa gagaaggaaa tacccaccgc tacggtcacc
acatggctag cttacacctt cgtgaatgaa gacgtaggga
ctataaaacc agtactagga gagagagtaa tccccgaccc
tgtagttgat atcaatttac aaccagaggt gcaagtggac
acgtcagagg ttgggatcac aataattgga agggaaaccc
```

-continued

```
tgatgacaac gggagtgaca cctgtcttgg aaaaagtaga
gcctgacgcc agcgacaacc aaaactcggt gaagatcggg
ttggatgagg gtaattaccc agggcctgga atacagacac
atacactaac agaagaaata cacaacaggg atgcgaggcc
cttcatcatg atcctgggct caaggaattc catatcaaat
agggcaaaga ctgctagaaa tataaatctg tacacaggaa
atgaccccag ggaaatacga gacttgatgg ctgcagggcg
catgttagta gtagcactga gggatgtcga ccctgagctg
tctgaaatgg tcgatttcaa ggggacttt ttagataggg
aggccctgga ggctctaagt ctcgggcaac ctaaaccgaa
gcaggttacc aaggaagctg ttaggaattt gatagaacag
aaaaaagatg tggagatccc taactggttt gcatcagatg
acccagtatt tctggaagtg gccttaaaaa atgataagta
ctacttagta ggagatgttg gagagctaaa agatcaagct
aaagcacttg gggccacgga tcagacaaga attataaagg
aggtaggctc aaggacgtat gccatgaagc tatctagctg
gttcctcaag gcatcaaaca aacagatgag tttaactcca
ctgtttgagg aattgttgct acggtgccca cctgcaacta
agagcaataa ggggcacatg gcatcagctt accaattggc
acagggtaac tgggagcccc tcggttgcgg ggtgcaccta
ggtacaatac cagccagaag ggtgaagata cacccatatg
aagcttacct gaagttgaaa gatttcatag aagaagaaga
gaagaaacct agggttaagg atacagtaat aagagagcac
aacaaatgga tacttaaaaa aataaggttt caaggaaacc
tcaacaccaa gaaaatgctc aacccaggga aactatctga
acagttggac agggaggggc gcaagaggaa catctacaac
caccagattg gtactataat gtcaagtgca ggcataaggc
tggagaaatt gccaatagtg agggcccaaa ccgacaccaa
aacctttcat gaggcaataa gagataagat agacaagagt
gaaaaccggc aaaatccaga attgcacaac aaattgttgg
agatttccca cacgatagcc caacccaccc tgaaacacac
ctacgtgag gtgacgtggg agcaacttga ggcgggggta
aatagaaagg gggcagcagg cttcctggaa aagaagaaca
tcggagaagt attggattca gaaaagcacc tggtagaaca
attggtcagg gatctgaagg ccgggagaaa gataaaatat
tatgaaactg caataccaaa aaatgagaag agagatgtca
gtgatgactg gcaggcaggg gacctggtgt tgagaagag
gccaagagtt atccaatacc ctgaagccaa gacaaggcta
gccatcacta aggtcatgta taactgggtg aaacagcagc
ccgttgtgat tccaggatat gaaggaaaga cccccttgtt
```

-continued

```
caacatcttt gataaagtga gaaaggaatg ggactcgttc
aatgagccag tggccgtaag ttttgacacc aaagcctggg
acactcaagt gactagtaag gatctgcaac ttattggaga
aatccagaaa tattactata agaaggagtg gcacaagttc
attgacacca tcaccgacca catgacagaa gtaccagtta
taacagcaga tggtgaagta tatataagaa atgggcagag
agggagcggc cagccagaca caagtgctgg caacagcatg
ttaaatgtcc tgacaatgat gtacggcttc tgcgaaagca
caggggtacc gtacaagagt ttcaacaggg tggcaaggat
ccacgtctgt ggggatgatg gcttcttaat aactgaaaaa
gggttagggc tgaaatttgc taacaaaggg atgcagattc
ttcatgaagc aggcaaacct cagaagataa cggaagggga
aaagatgaaa gttgcctata gatttgagga tatagagttc
tgttctcata ccccagtccc tgttaggtgg tccgacaaca
ccagtagtca catggccggg agagacaccg ctgtgatact
atcaaagatg caacaagat tggattcaag tggagagagg
ggtaccacag catatgaaaa agcggtagcc ttcagtttct
tgctgatgta ttcctggaac ccgcttgtta ggaggatttg
cctgttggtc ctttcgcaac agccagagac agacccatca
aaacatgcca cttattatta caaaggtgat ccaatagggg
cctataaaga tgtaataggt cggaatctaa gtgaactgaa
gagaacaggc tttgagaaat tggcaaatct aaacctaagc
ctgtccacgt tggggggtctg gactaagcac acaagcaaaa
gaataattca ggactgtgtt gccattggga agaagaggg
caactggcta gttaagcccg acaggctgat atccagcaaa
actggccact tatacatacc tgataaaggc tttacattac
aaggaaagca ttatgagcaa ctgcagctaa gaacagagac
aaacccggtc atggggggttg ggactgagag atacaagtta
ggtcccatag tcaatctgct gctgagaagg ttgaaaattc
tgctcatgac ggccgtcggc gtcagcagct gagacaaaat
gtatatattg taaataaatt aatccatgta catagtgtat
ataaatatag ttgggaccgt ccacctcaag aagacgacac
gcccaacacg cacagctaaa cagtagtcaa gattatctac
ctcaagataa cactacattt aatgcacaca gcactttagc
tgtatgagga tacgcccgac gtctatagtt ggactaggga
agacctctaa cag
                                  SEQ ID: 5
melitnelly ktykqkpvgv eepvydqagd plfgergavh
pqstlklphk rgerdvptnl aslpkrgdcr sgnsrgpvsg
iylkpgplfy qdykgpvyhr aplelfeegs mcettkrigr
vtgsdgklyh iyvcidgcii iksatrsyqr vfrwvhnrld
```

-continued

```
cplwvttcsd tkeegatkkk tqkpdrlerg kmkivpkese
kdsktkppda tivvegvkyq vrkkgktksk ntqdglyhnk
nkpqesrkkl ekallawaii aivlfqvtmg enitqwnlqd
ngtegiqram fqrgvnrslh giwpekictg vpshlatdie
lktihgmmda sektnytccr lqrhewnkhg wcnwyniepw
ilvmnrtqan ltegqpprec avtcrydras dlnvvtqard
sptpltgckk gknfsfagil mrgpcnfeia asdvlfkehe
rismfqdttl ylvdgltnsl egarqgtakl ttwlgkqlgi
lgkklenksk twfgayaasp ycdvdrkigy iwytknctpa
clpkntkivg pgkfgtnaed gkilhemggh lsevlllslv
vlsdfapeta svmylilhfs ipqshvdvmd cdktqlnltv
elttaevipg svwnlgkyvc irpnwwpyet tvvlafeevs
qvvklvlral rdltriwnaa tttaflvclv kivrgqmvqg
ilwlllitgv qghldckpef syaiakderi gqlgaegltt
twkeyspgmk ledtmviawc edgklmylqr ctretrylai
lhtralptsv vfkklfdgrk qedvvemndn fefglcpcda
kpivrgkfnt tllngpafqm vcpigwtgtv sctsfnmdtl
attvvrtyrr skpfphrqgc itqknlgedl hncilggnwt
cvpgdqllyk ggsiesckwc gyqfkesegl phypigkckl
enetgyrlvd stscnregva ivpqgtlkck igkttvqvia
mdtklgpmpc rpyeiisseg pvektactfn ytktlknkyf
eprdsyfqqy mlkgeyqywf dlevtdhhrd yfaesilvvv
vallggryvl wllvtymvls eqkalgiqyg sgevvmmgnl
lthnnievvt yflllylllr eesvkkwvll lyhilvvhpi
ksvivillmi gdvvkadsgg qeylgkidlc fttvvlivig
liiarrdpti vplvtimaal rvtelthqpg vdiavavmti
tllmvsyvtd yfrykkwlqc ilslvsavfl irsliylgri
empevtipnw rpltlillyl isttivtrwk vdvaglllqc
vpilllvttl wadfltlili lptyelvkly ylktvrtdte
rswlggidyt rvdsiydvde sgegvylfps rqkaqgnfsi
llplikatli scvsskwqli ymsyltldfm yymhrkviee
isggtniisr lvaalielnw smeeeeskgl kkfyllsgrl
rnliikhkvr netvaswyge eevygmpkim tiikastlsk
srhciictvc egrewkggtc pkcgrhgkpi tcgmsladfe
erhykrifir egnfegmcsr cqgkhrrfem drepksaryc
aecnrlhpae egdfwaessm lglkityfal mdgkvydite
wagcqrvgis pdthrvpchi sfgsrmpfrq eyngfvqyta
rgqlflrnlp vlatkvkmlm vgnlgeeign lehlgwilrg
pavckkiteh ekchinildk ltaffgimpr gttprapvrf
ptsllkvrrg letawaythq ggissvdhvt agkdllvcds
``` mgrtrvvcqs nnrltdetey gvktdsgcpd garcyvlnpe
avnisgskga vvhlqktgge ftcvtasgtp affdlknlkg
wsglpifeas sgrvvgrvkv gkneeskptk imsgiqtvsk
nradltemvk kitsmnrgdf kqitlatgag kttelpkavi
eeigrhkrvl vliplraaae svyqymrlkh psisfnlrig
dmkegdmatg ityasygyfc qmpqpklraa mveysyifld
eyhcatpeql aiigkihrfs esirvvamta tpagsvtttg
qkhpieefia pevmkgedlg sqfldiaglk ipvdemkgnm
lvfvptrnma vevakklkak gynsgyyysg edpanlrvvt
sqspyvivat naiesgvtlp dldtvidtgl kcekrvrvss
kipfivtglk rmavtvgeqa qrrgrvgrvk pgryyrsqet
atgskdyhyd llqaqrygie dginvtksfr emnydwslye
edsllitqle ilnnllised lpaavknima rtdhpepiql
aynsyevqvp vlfpkirnge vtdtyenysf lnarklgedv
pvyiyatede dlavdllgld wpdpgnqqvv etgkalkqvt
glssaenall valfgyvgyq alskrhvpmi tdiytiedqr
ledtthlqya pnaiktdgte telkelasgd vekimgaisd
yaagglefvk sqaekiktap lfkenaeaak gyvqkfidsl
ienkeeiiry glwgthtaly ksiaarlghe tafatlvlkw
lafggesvsd hvkqaavdlv vyyvmnkpsf pgdsetqqeg
rrfvaslfis alatytyktw nyhnlskvve palaylpyat
salkmftptr lesvvilstt iyktylsirk gksdgllgtg
isaameilsq npvsvgisvm lgvgaiaahn aiesseqkrt
llmkvfvknf ldqaatdelv kenpekiima lfeavqtign
plrliyhlyg vyykgweake lsertagrnl ftlimfeafe
llgmdsqgki rnlsgnyild liyglhkqin rglkkmvlgw
apapfscdwt psderirlpt dnylrvetrc pcgyemkafk
nvggkltkve esgpflcrnr pgrgpvnyrv tkyyddnlre
ikpvaklegq vehyykgvta kidyskgkml latdkweveh
gvitrlakry tgvgfngayl gdepnhralv erdcatitkn
tvqflkmkkg caftydltis nltrlielvh rnnleekeip
tatvttwlay tfvnedvgti kpvlgervip dpvvdinlqp
evqvdtsevg itiigretlm ttgvtpvlek vepdasdnqn
svkigldegn ypgpgiqtht lteeihnrda rpfimilgsr
nsisnrakta rninlytgnd preirdlmaa grmlvvalrd
vdpelsemvd fkgtfldrea lealslgqpk pkqvtkeavr
nlieqkkdve ipnwfasddp vflevalknd kyylvgdvge
lkdqakalga tdqtriikev gsrtyamkls swflkasnkq
msltplfeel llrcppatks nkghmasayq laqgnweplg
cgvhlgtipa rrvkihpyea ylklkdfiee eekkprvkdt -continued virehnkwil kkirfqgnln tkkmlnpgkl seqldregrk
rniynhqigt imssagirle klpivraqrd tktfheaird
kidksenrqn pelhnkllei fhtiaqptlk htygevtweq
leagvnrkga agflekknig evldsekhlv eqlvrdlkag
rkikyyetai pknekrdvsd dwqagdlvve krprviqype
aktrlaitkv mynwvkqqpv vipgyegktp lfnifdkvrk
ewdsfnepva vsfdtkawdt qvtskdlqli geiqkyyykk
ewhkfidtit dhmtevpvit adgevyirng qrgsgqpdts
agnsmlnvlt mmygfcestg vpyksfnrva rihvcgddgf
litekglglk fankgmqilh eagkpqkite gekmkvayrf
ediefcshtp vpvrwsdnts shmagrdtav ilskmatrld
ssgergttay ekavafsfll myswnplvrr icllvlsqqp
etdpskhaty yykgdpigay kdvigrnlse lkrtgfekla
nlnlslstlg vwtkhtskri iqdcvaigke egnwlvkpdr
lissktghly ipdkgftlqg khyeqlqlrt etnpvmgvgt
eryklgpivn lllrrlkill mtavgvss

SEQ ID NO: 6 melitnelly ktykqkpvgv eepvydqagn plfgergaih
pqstlklphk rgernvptsl aslpkrgdcr sgnskgpvsg
iylkpgplfy qdykgpvyhr aplelfeegs mcettkrigr
vtgsdgklyh iyicidgcit vksatrshqr vlrwvhnrld
cplwvtscsd tkeegatkkk qqkpdrlekg rmkivpkese
kdsktkppda tivvdgvkyq vkkkgkvksk ntqdglyhnk
nkppesrkkl ekallawail avvlievtmg enitqwnlqd
ngtegiqram fqrgvnrslh giwpekictg vpshlatdve
lktihgmmda sektnytccr lqrhewnkhg wcnwyniepw
ilimnrtqan ltegqpprec avtcrydrds dlnvvtqard
sptpltgckk gknfsfagvl trgpcnfeia asdvlfkehe
ctgvfqdtah ylvdgvtnsl esarqgtakl ttwlgkqlgi
lgkklenksk twfgayaasp ycdvdrkigy iwftknctpa
clpkntkiig pgkfdtnaed gkilhemggh lsevlllslv
vlsdfapeta samylilhfs ipqshvditd cdktqlnlti
elttadvipg svwnlgkyvc irpdwwpyet aavlafeevg
qvvkivlral rdltriwnaa tttaflvcli kmvrgqvvqg
ilwlllitgv qghldckpey syaiakndrv gplgaegltt
vwkdyshemk ledtmviawc kggkftylsr cttetrylai
lhsralptsv vfkklfegqk qedtvemddd fefglcpcda
kpivrgkfnt tllngpafqm vcpigwtgtv scmlanrdtl
dtavvrtyrr svpfpyrqgc irqktlgedl ydcalggnwt
cvtgdqsryt ggliesckwc gykfqksegl phypigkcrl -continued

```
nnetgyrlvd dtscdregva ivphglvkck igdttvqvia
tdtklgpmpc kpheiisseg piektactfn ytrtlknkyf
eprdsyfqqy mlkgdyqywf dlevtdhhrd yfaesilvvv
vallggryvl wllvtymvls eqkasgaqyg agevvmmgnl
lthdnvevvt yffllylllr eesvkkwvll lyhilvahpl
ksvivillmi gdvvkadpgg qgylgqidvc ftmvviiiig
liiarrdpti vplitivasl rvtgltyspg vdaamaviti
tllmvsyvtd yfrykrwlqc ilslvsgvfl irclihlgri
etpevtipnw rpltlilfyl isttvvtmwk idlaglllqg
vpilllittl wadfltlili lptyelvkly ylktiktdie
kswlggldyk rvdsiydvde sgegvylfps rqkaqknfsm
llplvratli scvsskwqli ymaylsvdfm yymhrkviee
isggtnmisr ivaalielnw smeeeeskgl kkfyllsgrl
rnliikhkvr netvagwyge eevygmpkim tiikastlnk
nkhciictvc egrkwkggtc pkcgrhgkpi tcgmsladfe
erhykrifir egnfegpfrq eyngfiqyta rgqlflrnlp
ilatkvkmlm vgnlgeevgd lehlgwilrg pavckkiteh
erchinildk ltaffgimpr gttprapvrf ptsllkvrrg
letgwaythq ggissvdhvt agkdllvcds mgrtrvvcqs
nnkltdetey gvktdsgcpd garcyvlnpe avnisgskga
vvhlqktgge ftcvtasgtp affdlknlkg wsglpifeas
sgrvvgrvkv gkneeskptk imsgiqtvsk ntadltemvk
kitsmnrgdf kqitlatgag kttelpkavi eeigrhkrvl
vliplraaae svyqymrlkh psisfnlrig dmkegdmatg
ityasygyfc qmpqpklraa mveysyifld eyhcatpeql
aiigkihrfs esirvvamta tpagsvtttg qkhpieefia
pevmegedlg sqfldiaglk ipvdemkgnm lvfvptrnma
vevakklkak gynsgyyysg edpanlrvvt sqspyvivat
naiesgvtlp dldtvvdtgl kcekrvrvss kipfivtglk
rmavtvgeqa qrrgrvgrvk pgryyrsqet atgskdyhyd
llqaqrygie dginvtksfr emnydwslye edsllitqle
ilnnllised lpaavknima rtdhpepiql aynsyevqvp
vlfpkirnge vtdtyenysf lnarklgedv pvyiyatede
dlavdllgld wpdpgnqqvv etgkalkqva glssaenall
valfgyvgyq alskrhvpmi tdiytiedqr ledtthlqya
pnaiktegte telkelasgd vekimgaisd yaaggldfvk
sqaekiktap lfkenveaar gyvqklidsl iedkdviiry
glwgthtaly ksiaarlghe tafatlvlkw lafggetvsd
hirqaavdlv vyyvmnkpsf pgdtetqqeg rrfvaslfis
-continued
```
alatytyktw nynnlskvve palaylpyat salkmftptr
lesvvilstt iyktylsirk gksdgllgtg isaameilsq
npvsvgisvm lgvgaiaahn aiesseqkrt llmkvfvknf
ldqaatdelv kenpekiima lfeavqtign plrliyhlyg
vyykgweake lsertagrnl ftlimfeafe llgmdsegki
rnlsgnyild lihglhkqin rglkkivlgw apapfscdwt
psderirlpt dsylrvetkc pcgyemkalk nvsgkltkve
esgpflcrnr pgrgpvnyrv tkyyddnlre irpvaklegq
vehyykgvta ridyskgktl latdkweveh gtltrltkry
tgvgfrgayl gdepnhrdlv erdcatitkn tvqflkmkkg
caftydlris nltrlielvh rnnleekeip tatvttwlay
tfvnedvgti kpvlgervip dpvvdinlqp evqvdtsevg
itiigkeavm ttgvtpvmek vepdtdnnqs svkigldegn
ypgpgvqtht lveeihnkda rpfimvlgsk ssmsnrakta
rninlytgnd preirdlmae grilvvalrd idpdlselvd
fkgtfldrea lealslgqpk pkqvtkaair dllkeerqve
ipdwftsddp vfldiamkkd kyhligdvve vkdqakalga
tdqtrivkev gsrtytmkls swflqasskq msltplfeel
llrcppatks nkghmasayq laqqnweplg cgvhlgtvpa
rrvkmhpyea ylklkdlvee eekkprirdt virehnkwil
kkikfqgnln tkkmlnpgkl seqldreghk rniynnqist
vmssagirle klpivraqtd tksfheaird kidknenrqn
pelhnkllei fhtiadpslk hrygevtweq leaginrkga
agflekknig evldsekhlv eqlvrdlkag rkiryyetai
pknekrdvsd dwqagdlvde kkprviqype aktrlaitkv
mynwvkqqpv vipgyegktp lfnifnkvrk ewdlfnepva
vsfdtkawdt qvtsrdlhli geiqkyyyrk ewhkfidtit
dhmvevpvit adgevyirng qrgsgqpdts agnsmlnvlt
miyafcestg vpyksfnrva kihvcgddgf litekglglk
fsnkgmqilh eagkpqklte gekmkvaykf ediefcshtp
vpvrwsdnts symagrdtav ilskmatrld ssgergttay
ekavafsfll myswnplvrr icllvlsqrp etapstqtty
yykgdpigay kdvigrnlse lkrtgfekla nlnlslstlg
iwtkhtskri iqdcvaigke egnwlvnadr lissktghly -continued lllrrlkvll maavgass

SEQ ID NO: 7 cgtggcttcttggtacggg

SEQ ID NO: 8 agcggtatattgtacaaagcca

SEQ ID NO: 9 tgcacgatctgtgaagggaaagaa

SEQ ID NO: 10 tgcactgtatgtgagggccgagag

---

What is claimed is:

1. A vaccine comprising at least two live mutant viruses, wherein said viruses comprise a mutant cytopathic (cp) Bovine Viral Diarrhea Virus Type 1 (cp BVDV-1) and a mutant cytopathic Bovine Viral Diarrhea Virus Type 2 (cp BVDV-2), wherein the cp BVDV-1 and the cp BVDV-2 each contains a mutation in the viral genome that resides in the same genomic site such that said cp BVDV-1 and said cp BVDV-2 cannot recombine with each other to eliminate the mutations, and further wherein said cp BVDV-1 and cp BVDV-2 are both attenuated.

2. The vaccine of claim 1, wherein the cp BVDV-1 and the cp BVDV-2 both comprise a mutation in the NS2-3 region that results in a cytopathic biotype.

3. The vaccine of claim 2, wherein said mutation comprises an insertion of a heterologous sequence.

4. The vaccine of claim 1, further comprising at least one of bovine herpesvirus-1, bovine respiratory syncytial virus, parainfluenza virus-3, *Campylobacter fetus, Leptospira canicola, Leptospira grippotyphosa, Leptospira hardjo, Leptospira icterohaemorrhagiae, Leptospira pomona*, or *Mannhemia haemolytica*.

5. The vaccine as in claim 1 or claim 4, further comprising a veterinarily-acceptable carrier.

6. The vaccine of claim 5, wherein said veterinarily-acceptable carrier comprises an oil-in-water emulsion.

* * * * *

SEQUENCE LISTING

<160> NUMBER OF SEQ ID NOS: 18

<210> SEQ ID NO 1
<211> LENGTH: 19
<212> TYPE: DNA
<213> ORGANISM: Artificial sequence
<220> FEATURE:
<223> OTHER INFORMATION: synthetic oligonucleotide forward primer
      53637U1

<400> SEQUENCE: 1
cgtccacaga tggtttggt                                              19

<210> SEQ ID NO 2
<211> LENGTH: 22
<212> TYPE: DNA
<213> ORGANISM: Artificial sequence
<220> FEATURE:
<223> OTHER INFORMATION: synthetic reverse primer 53637L

<400> SEQUENCE: 2
ggctatgtat tggacgtaac cc                                          22

<210> SEQ ID NO 3
<211> LENGTH: 670
<212> TYPE: DNA
<213> ORGANISM: Pestivirus bovine viral diarrhea virus 2
<220> FEATURE:
<221> NAME/KEY: misc_feature
<223> OTHER INFORMATION: Bovine Viral Diarrhea Virus 2 strain 53637

<400> SEQUENCE: 3
cgtccacaga tggtttggtg aggaggaaat atatggggca cccaaggtga tcaccatcat     60
aaaagctagt accctaagta aaaacaggca ctgcataatc tgcacgatct gtgaagggaa    120
agaatggaac ggagccaact gcccaaagtg tggaagacaa ggaaagccca taacatgtgg    180
aatgacactc gcagactttg aggagaaaca ttacaaaaag atatttataa gagaaggacg    240
ccaagaagca atgaatacga tgatgtgcag ccgatgccag ggaaagcata ggaggtttga    300
aacggaccgg gaacctaaga gtgccagata ctgtgctgag tgtaataggc tgcatcctgc    360
tgaggaaggt gacttttggg cagagtcaag catgttgggc ctcaaaatca cctactttgc    420
gctgatggat ggaaaggtgt atgatatcac agagtgggct ggatgccagc gtgtgggaat    480
ctccccagat acccacagag tcccttgtca catctcattt ggttcacgga tgccaggcac    540
cagtgggcgg cagagagcta ctccagatgc ccctcctgct gaccttcagg atttcttgag    600
ccggatcttt caagtacccc caggccagat gtccagggaa gagtataagg gttacgtcca    660
atacatagcc                                                          670

<210> SEQ ID NO 4

<211> LENGTH: 12573
<212> TYPE: DNA
<213> ORGANISM: Pestivirus bovine viral diarrhea virus 1
<220> FEATURE:
<221> NAME/KEY: misc_feature
<223> OTHER INFORMATION: bovine viral diarrhea virus 1 strain NADL

<400> SEQUENCE: 4

| | | | | | |
|---|---|---|---|---|---|
| gtatacgaga | attagaaaag | gcactcgtat | acgtattggg | caattaaaaa | taataattag | 60 |
| gcctagggaa | caaatccctc | tcagcgaagg | ccgaaaagag | gctagccatg | cccttagtag | 120 |
| gactagcata | atgaggggg | tagcaacagt | ggtgagttcg | ttggatggct | taagccctga | 180 |
| gtacagggta | gtcgtcagtg | gttcgacgcc | ttggaataaa | ggtctcgaga | tgccacgtgg | 240 |
| acgagggcat | gcccaaagca | catcttaacc | tgagcggggg | tcgcccaggt | aaaagcagtt | 300 |
| ttaaccgact | gttacgaata | cagcctgata | gggtgctgca | gaggcccact | gtattgctac | 360 |
| taaaaatctc | tgctgtacat | ggcacatgga | gttgatcaca | aatgaacttt | tatacaaaac | 420 |
| atacaaacaa | aaacccgtcg | gggtggagga | acctgtttat | gatcaggcag | gtgatccctt | 480 |
| atttggtgaa | aggggagcag | tccaccctca | atcgacgcta | aagctcccac | acaagagagg | 540 |
| ggaacgcgat | gttccaacca | acttggcatc | cttaccaaaa | agaggtgact | gcaggtcggg | 600 |
| taatagcaga | ggacctgtga | gcgggatcta | cctgaagcca | gggccactat | tttaccagga | 660 |
| ctataaaggt | cccgtctatc | acagggcccc | gctggagctc | tttgaggagg | gatccatgtg | 720 |
| tgaaacgact | aaacgggatag | ggagagtaac | tggaagtgac | ggaaagctgt | accacattta | 780 |
| tgtgtgtata | gatggatgta | taataataaa | aagtgccacg | agaagttacc | aaagggtgtt | 840 |
| caggtgggtc | cataataggc | ttgactgccc | tctatgggtc | acaacttgct | cagacacgaa | 900 |
| agaagaggga | gcaacaaaaa | agaaaacaca | gaaacccgac | agactagaaa | ggggaaaat | 960 |
| gaaaatagtg | cccaaagaat | ctgaaaaga | cagcaaaact | aaacctccgg | atgctacaat | 1020 |
| agtggtggaa | ggagtcaaat | accaggtgag | gaagaaggga | aaaccaaga | gtaaaaacac | 1080 |
| tcaggacggc | ttgtaccata | acaaaaacaa | acctcaggaa | tcacgcaaga | aactggaaaa | 1140 |
| agcattgttg | gcgtgggcaa | taatagctat | agttttgttt | caagttacaa | tgggagaaaa | 1200 |
| cataacacag | tggaacctac | aagataatgg | gacggaaggg | atacaacggg | caatgttcca | 1260 |
| aagggggtgtg | aatagaagtt | tacatggaat | ctggccagaa | aaaatctgta | ctggcgtccc | 1320 |
| ttcccatcta | gccaccgata | tagaactaaa | aacaattcat | ggtatgatgg | atgcaagtga | 1380 |
| gaagaccaac | tacacgtgtt | gcagacttca | acgccatgag | tggaacaagc | atggttggtg | 1440 |
| caactggtac | aatattgaac | cctggattct | agtcatgaat | agaacccaag | ccaatctcac | 1500 |
| tgagggacaa | ccaccaaggg | agtgcgcagt | cacttgtagg | tatgataggg | ctagtgactt | 1560 |
| aaacgtggta | acacaagcta | gagatagccc | cacaccctta | acaggttgca | agaaaggaaa | 1620 |
| gaacttctcc | tttgcaggca | tattgatgcg | ggggccctgc | aactttgaaa | tagctgcaag | 1680 |
| tgatgtatta | ttcaaagaac | atgaacgcat | tagtatgttc | caggatacca | ctctttacct | 1740 |
| tgttgacggg | ttgaccaact | ccttagaagg | tgccagacaa | ggaaccgcta | aactgacaac | 1800 |
| ctggttaggc | aagcagctcg | ggatactagg | aaaaaagttg | gaaaacaaga | gtaagacgtg | 1860 |
| gtttggagca | tacgctgctt | cccccttactg | tgatgtcgat | cgcaaaattg | gctacatatg | 1920 |
| gtatacaaaa | aattgcaccc | ctgcctgctt | acccaagaac | acaaaaattg | tcggccctgg | 1980 |
| gaaatttggc | accaatgcag | aggacggcaa | gatattacat | gagatggggg | gtcacttgtc | 2040 |
| ggaggtacta | ctactttctt | tagtggtgct | gtccgacttc | gcaccggaaa | cagctagtgt | 2100 |

```
aatgtaccta atcctacatt tttccatccc acaaagtcac gttgatgtaa tggattgtga    2160
taagacccag ttgaacctca cagtggagct gacaacagct gaagtaatac cagggtcggt    2220
ctggaatcta ggcaaatatg tatgtataag accaaattgg tggccttatg agacaactgt    2280
agtgttggca tttgaagagg tgagccaggt ggtgaagtta gtgttgaggg cactcagaga    2340
tttaacacgc atttggaacg ctgcaacaac tactgctttt ttagtatgcc ttgttaagat    2400 agtcagggc cagatggtac agggcattct gtggctacta ttgataacag ggtacaagg     2460 gcacttggat tgcaaacctg aattctcgta tgccatagca aaggacgaaa gaattggtca    2520
actgggggct gaaggcctta ccaccacttg aaggaatac tcacctggaa tgaagctgga     2580
agacacaatg gtcattgctt ggtgcgaaga tgggaagtta atgtacctcc aaagatgcac    2640
gagagaaacc agatatctcg caatcttgca tacaagagcc ttgccgacca gtgtggtatt    2700
caaaaaactc tttgatgggc gaaagcaaga ggatgtagtc gaaatgaacg acaactttga    2760
atttggactc tgcccatgtg atgccaaacc catagtaaga gggaagttca atacaacgct    2820
gctgaacgga ccggccttcc agatggtatg ccccatagga tggacaggga ctgtaagctg    2880
tacgtcattc aatatggaca ccttagccac aactgtggta cggacatata aaggtctaa    2940 accattccct cataggcaag gctgtatcac ccaaaagaat ctgggggagg atctccataa    3000
ctgcatcctt ggaggaaatt ggacttgtgt gcctggagac caactactat acaaggggg    3060 ctctattgaa tcttgcaagt ggtgtggcta tcaatttaaa gagagtgagg gactaccaca    3120
ctaccccatt ggcaagtgta aattggagaa cgagactggt tacaggctag tagacagtac    3180
ctcttgcaat agagaaggtg tggccatagt accacaaggg acattaaagt gcaagatagg    3240
aaaaacaact gtacaggtca tagctatgga taccaaactc ggacctatgc cttgcagacc    3300
atatgaaatc atatcaagtg aggggcctgt agaaaagaca gcgtgtactt tcaactacac    3360
taagacatta aaaaataagt attttgagcc cagagacagc tactttcagc aatacatgct    3420
aaaaggagag tatcaatact ggtttgacct ggaggtgact gaccatcacc gggattactt    3480
cgctgagtcc atattagtgg tggtagtagc cctcttgggt ggcagatatg tactttggtt    3540
actggttaca tacatggtct tatcagaaca gaaggcctta gggattcagt atggatcagg    3600
ggaagtggtg atgatgggca acttgctaac ccataacaat attgaagtgg tgacatactt    3660
cttgctgctg tacctactgc tgagggagga gagcgtaaag aagtgggtct tactcttata    3720
ccacatctta gtggtacacc caatcaaatc tgtaattgtg atcctactga tgattgggga    3780
tgtggtaaag gccgattcag ggggccaaga gtacttgggg aaaatagacc tctgttttac    3840
aacagtagta ctaatcgtca taggtttaat catagctagg cgtgacccaa ctatagtgcc    3900
actggtaaca ataatggcag cactgagggt cactgaactg acccaccagc tggagttga    3960 catcgctgtg gcggtcatga ctataaccct actgatggtt agctatgtga cagattattt    4020
tagatataaa aaatgttac agtgcattct cagcctggta tctgcggtgt tcttgataag    4080
aagcctaata tacctaggta gaatcgagat gccagaggta actatcccaa actggagacc    4140 actaactta atactattat atttgatctc aacaacaatt gtaacgaggt ggaaggttga    4200
cgtggctggc ctattgttgc aatgtgtgcc tatcttattg ctggtcacaa ccttgtgggc    4260
cgacttctta accctaatac tgatcctgcc tacctatgaa ttggttaaat tatactatct    4320
gaaaactgtt aggactgata cagaaagaag ttggctaggg gggatagact atacaagagt    4380
tgactccatc tacgacgttg atgagagtgg agagggcgta tatctttttc catcaaggca    4440
gaaagcacag gggaattttt ctatactctt gccccttatc aaagcaacac tgataagttg    4500
```

```
cgtcagcagt aaatggcagc taatatacat gagttactta actttggact ttatgtacta    4560
catgcacagg aaagttatag aagagatctc aggaggtacc aacataatat ccaggttagt    4620
ggcagcactc atagagctga actggtccat ggaagaagag gagagcaaag cttaaagaa    4680 gttttatcta ttgtctggaa ggttgagaaa cctaataata aaacataagg taaggaatga    4740
gaccgtggct tcttggtacg gggaggagga agtctacggt atgccaaaga tcatgactat    4800
aatcaaggcc agtacactga gtaagagcag gcactgcata atatgcactg tatgtgaggg    4860
ccgagagtgg aaaggtggca cctgcccaaa atgtggacgc catgggaagc cgataacgtg    4920
tgggatgtcg ctagcagatt ttgaagaaag acactataaa agaatcttta taagggaagg    4980
caactttgag ggtatgtgca gccgatgcca gggaaagcat aggaggtttg aaatggaccg    5040
ggaacctaag agtgccagat actgtgctga gtgtaatagg ctgcatcctg ctgaggaagg    5100
tgacttttgg gcagagtcga gcatgttggg cctcaaaatc acctactttg cgctgatgga    5160
tggaaaggtg tatgatatca cagagtgggc tggatgccag cgtgtgggaa tctccccaga    5220
tacccacaga gtcccttgtc acatctcatt tggttcacgg atgccttttca ggcaggaata    5280 caatggcttt gtacaatata ccgctagggg gcaactattt ctgagaaact tgcccgtact    5340
ggcaactaaa gtaaaaatgc tcatggtagg caaccttgga gaagaaattg gtaatctgga    5400
acatcttggg tggatcctaa gggggcctgc cgtgtgtaag aagatcacag agcacgaaaa    5460
atgccacatt aatatactgg ataaactaac cgcatttttc gggatcatgc caaggggggac    5520 tacacccaga gccccggtga ggttccctac gagcttacta aaagtgagga ggggtctgga    5580
gactgcctgg gcttacacac accaaggcgg gataagttca gtcgaccatg taaccgccgg    5640
aaaagatcta ctggtctgtg acagcatggg acgaactaga gtggtttgcc aaaagcaacaa    5700 caggttgacc gatgagacag agtatggcgt caagactgac tcagggtgcc cagacggtgc    5760
cagatgttat gtgttaaatc cagaggccgt taacatatca ggatccaaag gggcagtcgt    5820
tcacctccaa aagacaggtg gagaattcac gtgtgtcacc gcatcaggca caccggcttt    5880
cttcgaccta aaaaacttga aaggatggtc aggcttgcct atatttgaag cctccagcgg    5940
gagggtggtt ggcagagtca agtagggaa gaatgaagag tctaaaccta caaaaataat    6000
gagtggaatc cagaccgtct caaaaaacag agcagacctg accgagatgg tcaagaagat    6060
aaccagcatg aacaggggag acttcaagca gattactttg gcaacagggg caggcaaaac    6120
cacagaactc ccaaaagcag ttatagagga gataggaaga cacaagagag tattagttct    6180
tataccatta agggcagcgg cagagtcagt ctaccagtat atgagattga acacccaag     6240 catctctttt aacctaagga taggggacat gaaagagggg gacatggcaa ccgggataac    6300
ctatgcatca tacgggtact tctgccaaat gcctcaacca aagctcagag ctgctatggt    6360
agaatactca tacatattct tagatgaata ccattgtgcc actcctgaac aactggcaat    6420
tatcgggaag atccacagat tttcagagag tataagggtt gtcgccatga ctgccacgcc    6480
agcagggtcg gtgaccacaa caggtcaaaa gcacccaata gaggaattca tagcccccga    6540
ggtaatgaaa ggggaggatc ttggtagtca gttccttgat atagcagggt aaaaatacc    6600 agtggatgag atgaaaggca atatgttggt ttttgtacca acgagaaaca tggcagtaga    6660
ggtagcaaag aagctaaaag ctaagggcta taactctgga tactattaca gtggagagga    6720
tccagccaat ctgagagttg tgacatcaca atccccctat gtaatcgtgg ctacaaatgc    6780
tattgaatca ggagtgacac taccagattt ggacacggtt atagacacgg ggttgaaatg    6840
```

```
tgaaaagagg gtgagggtat catcaaagat acccttcatc gtaacaggcc ttaagaggat    6900
ggccgtgact gtgggtgagc aggcgcagcg tagggggcaga gtaggtagag tgaaacccgg    6960
gaggtattat aggagccagg aaacagcaac agggtcaaag gactaccact atgacctctt    7020
gcaggcacaa agatacggga ttgaggatgg aatcaacgtg acgaaatcct ttagggagat    7080
gaattacgat tggagcctat acgaggagga cagcctacta ataacccagc tggaaatact    7140
aaataatcta ctcatctcag aagacttgcc agccgctgtt aagaacataa tggccaggac    7200
tgatcaccca gagccaatcc aacttgcata caacagctat gaagtccagg tcccggtcct    7260
attcccaaaa ataaggaatg gagaagtcac agacacctac gaaaattact cgtttctaaa    7320
tgccagaaag ttaggggagg atgtgcccgt gtatatctac gctactgaag atgaggatct    7380
ggcagttgac ctcttaggc tagactggcc tgatcctggg aaccagcagg tagtggagac    7440
tggtaaagca ctgaagcaag tgaccgggtt gtcctcggct gaaaatgccc tactagtggc    7500
tttatttggg tatgtgggtt accaggctct ctcaaagagg catgtcccaa tgataacaga    7560
catatatacc atcgaggacc agagactaga agacaccacc cacctccagt atgcacccaa    7620
cgccataaaa accgatggga cagagactga actgaaagaa ctggcgtcgg gtgacgtgga    7680
aaaaatcatg ggagccattt cagattatgc agctggggga ctggagtttg ttaaatccca    7740
agcagaaaag ataaaaacag ctcctttgtt taaagaaaac gcagaagccg caaaagggta    7800
tgtccaaaaa ttcattgact cattaattga aaataaagaa gaaataatca gatatggttt    7860
gtggggaaca cacacagcac tatacaaaag catagctgca agactggggc atgaaacagc    7920
gtttgccaca ctagtgttaa agtggctagc ttttggaggg gaatcagtgt cagaccacgt    7980
caagcaggcg gcagttgatt tagtggtcta ttatgtgatg aataagcctt ccttcccagg    8040
tgactccgag acacagcaag aagggaggcg attcgtcgca agcctgttca tctccgcact    8100
ggcaacctac acatacaaaa cttggaatta ccacaatctc tctaaagtgg tggaaccagc    8160
cctggcttac ctcccctatg ctaccagcgc attaaaaatg ttcaccccaa cgcggctgga    8220
gagcgtggtg atactgagca ccacgatata taaaacatac ctctctataa ggaaggggaa    8280
gagtgatgga ttgctgggta cggggataag tgcagccatg gaaatcctgt cacaaaaccc    8340
agtatcggta ggtatatctg tgatgttggg ggtaggggca atcgctgcgc acaacgctat    8400
tgagtccagt gaacagaaaa ggaccctact tatgaaggtg tttgtaaaga acttcttgga    8460
tcaggctgca acagatgagc tggtaaaaga aaacccagaa aaaattataa tggccttatt    8520
tgaagcagtc cagacaattg gtaacccct gagactaata taccacctgt atggggttta    8580
ctacaaaggt tgggaggcca aggaactatc tgagaggaca gcaggcagaa acttattcac    8640
attgataatg tttgaagcct tcgagttatt agggatggca tcacaaggga aaataaggaa    8700
cctgtccgga aattacattt tggatttgat atacggccta cacaagcaaa tcaacagagg    8760
gctgaagaaa atggtactgg ggtgggcccc tgcacccttt agttgtgact ggaccccctag    8820 tgacgagagg atcagattgc caacagacaa ctatttgagg gtagaaacca ggtgcccatg    8880
tggctatgag atgaaagctt tcaaaaatgt aggtggcaaa cttaccaaag tggaggagag    8940
cgggcctttc ctatgtagaa acagacctgg taggggacca gtcaactaca gagtcaccaa    9000
gtattacgat gacaacctca gagagataaa accagtagca aagttggaag acaggtagaa    9060
gcactactac aaaggggtca cagcaaaaat tgactacagt aaaggaaaaa tgctcttggc    9120
cactgacaag tgggaggtgg aacatggtgt cataaccagg ttagctaaga gatatactgg    9180
ggtcgggttc aatggtgcat acttaggtga cgagcccaat caccgtgctc tagtggagag    9240
```

```
ggactgtgca actataacca aaaacacagt acagtttcta aaaatgaaga agggggtgtgc    9300
gttcacctat gacctgacca tctccaatct gaccaggctc atcgaactag tacacaggaa    9360
caatcttgaa gagaaggaaa tacccaccgc tacggtcacc acatggctag cttacacctt    9420
cgtgaatgaa gacgtaggga ctataaaacc agtactagga gagagagtaa tccccgaccc    9480
tgtagttgat atcaatttac aaccagaggt gcaagtggac acgtcagagg ttgggatcac    9540
aataattgga agggaaaccc tgatgacaac gggagtgaca cctgtcttgg aaaaagtaga    9600
gcctgacgcc agcgacaacc aaaactcggt gaagatcggg ttggatgagg gtaattaccc    9660
agggcctgga atacagacac atacactaac agaagaaata cacaacaggg atgcgaggcc    9720
cttcatcatg atcctgggct caaggaattc catatcaaat agggcaaaga ctgctagaaa    9780
tataaatctg tacacaggaa atgaccccag ggaaatacga gacttgatgg ctgcagggcg    9840
catgttagta gtagcactga gggatgtcga ccctgagctg tctgaaatgg tcgatttcaa    9900
ggggacttt ttagataggg aggccctgga ggctctaagt ctcgggcaac ctaaaccgaa    9960
gcaggttacc aaggaagctg ttaggaattt gatagaacag aaaaaagatg tggagatccc   10020
taactggttt gcatcagatg acccagtatt tctggaagtg gccttaaaaa atgataagta   10080
ctacttagta ggagatgttg gagagctaaa agatcaagct aaagcacttg gggccacgga   10140
tcagacaaga attataaagg aggtaggctc aaggacgtat gccatgaagc tatctagctg   10200
gttcctcaag gcatcaaaca acagatgag tttaactcca ctgtttgagg aattgttgct   10260
acggtgccca cctgcaacta gagcaataa ggggcacatg gcatcagctt accaattggc   10320
acagggtaac tggagccccc tcggttgcgg ggtgcaccta ggtacaatac cagccagaag   10380
ggtgaagata cacccatatg aagcttacct gaagttgaaa gatttcatag aagaagaaga   10440
gaagaaacct agggttaagg atacagtaat aagagagcac aacaaatgga tacttaaaaa   10500
aataaggttt caaggaaacc tcaacaccaa gaaaatgctc aacccaggga aactatctga   10560
acagttggac agggaggggc gcaagaggaa catctacaac caccagattg gtactataat   10620
gtcaagtgca ggcataaggc tggagaaaat gccaatagtg agggcccaaa ccgacaccaa   10680
aacctttcat gaggcaataa gagataagat agacaagagt gaaaaccggc aaaatccaga   10740
attgcacaac aaattgttgg agattttcca cacgatagcc caaccacccc tgaaacacac   10800
ctacggtgag gtgacgtggg agcaacttga ggcgggggta aatagaaagg gggcagcagg   10860
cttcctggaa aagaagaaca tcggagaagt attggattca gaaaagcacc tggtagaaca   10920
attggtcagg gatctgaagg ccgggagaaa gataaaatat tatgaaactg caataccaaa   10980
aaatgagaag agagatgtca gtgatgactg gcaggcaggg gacctggtgg ttgagaagag   11040
gccaagagtt atccaatacc ctgaagccaa gacaaggcta gccatcacta aggtcatgta   11100
taactgggtg aaacagcagc ccgttgtgat tccaggatat gaaggaaaga ccccttgtt   11160
caacatcttt gataaagtga gaaaggaatg ggactcgttc aatgagccag tggccgtaag   11220
ttttgacacc aaagcctggg acactcaagt gactagtaag gatctgcaac ttattggaga   11280
aatccagaaa tattactata agaaggagtg gcacaagttc attgacacca tcaccgacca   11340
catgacagaa gtaccagtta acagcaga tggtgaagta tatataagaa atgggcagag   11400
agggagcggc cagccagaca caagtgctgg caacagcatg ttaaatgtcc tgacaatgat   11460
gtacggcttc tgcgaaagca caggggtacc gtacaagagt ttcaacgggg tggcaaggat   11520
ccacgtctgt ggggatgatg gcttcttaat aactgaaaaa gggttagggc tgaaatttgc   11580
```

-continued

```
taacaaaggg atgcagattc ttcatgaagc aggcaaacct cagaagataa cggaagggga    11640
aaagatgaaa gttgcctata gatttgagga tatagagttc tgttctcata ccccagtccc    11700
tgttaggtgg tccgacaaca ccagtagtca catggccggg agagacaccg ctgtgatact    11760
atcaaagatg gcaacaagat tggattcaag tggagagagg ggtaccacag catatgaaaa    11820
agcggtagcc ttcagtttct tgctgatgta ttcctggaac ccgcttgtta ggaggatttg    11880
cctgttggtc ctttcgcaac agccagagac agacccatca aaacatgcca cttattatta    11940
caaaggtgat ccatagggg cctataaaga tgtaataggt cggaatctaa gtgaactgaa    12000
gagaacaggc tttgagaaat tggcaaatct aaacctaagc ctgtccacgt tgggggtctg    12060
gactaagcac acaagcaaaa gaataattca ggactgtgtt gccattggga agaagaggg    12120 caactggcta gttaagcccg acaggctgat atccagcaaa actggccact tatacatacc    12180
tgataaaggc tttacattac aaggaaagca ttatgagcaa ctgcagctaa gaacagagac    12240
aaacccggtc atgggggttg ggactgagag atacaagtta ggtcccatag tcaatctgct    12300
gctgagaagg ttgaaaattc tgctcatgac ggccgtcggc gtcagcagct gagacaaaat    12360
gtatatattg taaataaatt aatccatgta catagtgtat ataaatatag ttgggaccgt    12420
ccacctcaag aagacgacac gcccaacacg cacagctaaa cagtagtcaa gattatctac    12480
ctcaagataa cactacattt aatgcacaca gcactttagc tgtatgagga tacgcccgac    12540
gtctatagtt ggactaggga agacctctaa cag                                 12573
```

<210> SEQ ID NO 5
<211> LENGTH: 3988
<212> TYPE: PRT
<213> ORGANISM: Pestivirus bovine viral diarrhea virus 1
<220> FEATURE:
<221> NAME/KEY: misc_feature
<223> OTHER INFORMATION: Bovine Viral Diarrhea Virus 1 strain NADL

<400> SEQUENCE: 5

```
Met Glu Leu Ile Thr Asn Glu Leu Leu Tyr Lys Thr Tyr Lys Gln Lys
1               5                   10                  15

Pro Val Gly Val Glu Pro Val Tyr Asp Gln Ala Gly Asp Pro Leu
            20                  25                  30

Phe Gly Glu Arg Gly Ala Val His Pro Gln Ser Thr Leu Lys Leu Pro
        35                  40                  45

His Lys Arg Gly Glu Arg Asp Val Pro Thr Asn Leu Ala Ser Leu Pro
    50                  55                  60

Lys Arg Gly Asp Cys Arg Ser Gly Asn Ser Arg Gly Pro Val Ser Gly
65                  70                  75                  80

Ile Tyr Leu Lys Pro Gly Pro Leu Phe Tyr Gln Asp Tyr Lys Gly Pro
                85                  90                  95

Val Tyr His Arg Ala Pro Leu Glu Leu Phe Glu Glu Gly Ser Met Cys
            100                 105                 110

Glu Thr Thr Lys Arg Ile Gly Arg Val Thr Gly Ser Asp Gly Lys Leu
        115                 120                 125

Tyr His Ile Tyr Val Cys Ile Asp Gly Cys Ile Ile Lys Ser Ala
    130                 135                 140

Thr Arg Ser Tyr Gln Arg Val Phe Arg Trp Val His Asn Arg Leu Asp
145                 150                 155                 160

Cys Pro Leu Trp Val Thr Thr Cys Ser Asp Thr Lys Glu Glu Gly Ala
                165                 170                 175

Thr Lys Lys Lys Thr Gln Lys Pro Asp Arg Leu Glu Arg Gly Lys Met
```

-continued

```
            180                 185                 190
Lys Ile Val Pro Lys Glu Ser Glu Lys Asp Ser Lys Thr Lys Pro Pro
                195                 200                 205

Asp Ala Thr Ile Val Val Glu Gly Val Lys Tyr Gln Val Arg Lys Lys
            210                 215                 220

Gly Lys Thr Lys Ser Lys Asn Thr Gln Asp Gly Leu Tyr His Asn Lys
225                 230                 235                 240

Asn Lys Pro Gln Glu Ser Arg Lys Lys Leu Glu Lys Ala Leu Leu Ala
                245                 250                 255

Trp Ala Ile Ile Ala Ile Val Leu Phe Gln Val Thr Met Gly Glu Asn
            260                 265                 270

Ile Thr Gln Trp Asn Leu Gln Asp Asn Gly Thr Glu Gly Ile Gln Arg
                275                 280                 285

Ala Met Phe Gln Arg Gly Val Asn Arg Ser Leu His Gly Ile Trp Pro
            290                 295                 300

Glu Lys Ile Cys Thr Gly Val Pro Ser His Leu Ala Thr Asp Ile Glu
305                 310                 315                 320

Leu Lys Thr Ile His Gly Met Met Asp Ala Ser Glu Lys Thr Asn Tyr
                325                 330                 335

Thr Cys Cys Arg Leu Gln Arg His Glu Trp Asn Lys His Gly Trp Cys
            340                 345                 350

Asn Trp Tyr Asn Ile Glu Pro Trp Ile Leu Val Met Asn Arg Thr Gln
                355                 360                 365

Ala Asn Leu Thr Glu Gly Gln Pro Pro Arg Glu Cys Ala Val Thr Cys
            370                 375                 380

Arg Tyr Asp Arg Ala Ser Asp Leu Asn Val Val Thr Gln Ala Arg Asp
385                 390                 395                 400

Ser Pro Thr Pro Leu Thr Gly Cys Lys Lys Gly Lys Asn Phe Ser Phe
                405                 410                 415

Ala Gly Ile Leu Met Arg Gly Pro Cys Asn Phe Glu Ile Ala Ala Ser
            420                 425                 430

Asp Val Leu Phe Lys Glu His Glu Arg Ile Ser Met Phe Gln Asp Thr
            435                 440                 445

Thr Leu Tyr Leu Val Asp Gly Leu Thr Asn Ser Leu Glu Gly Ala Arg
450                 455                 460

Gln Gly Thr Ala Lys Leu Thr Thr Trp Leu Gly Lys Gln Leu Gly Ile
465                 470                 475                 480

Leu Gly Lys Lys Leu Glu Asn Lys Ser Lys Thr Trp Phe Gly Ala Tyr
                485                 490                 495

Ala Ala Ser Pro Tyr Cys Asp Val Asp Arg Lys Ile Gly Tyr Ile Trp
            500                 505                 510

Tyr Thr Lys Asn Cys Thr Pro Ala Cys Leu Pro Lys Asn Thr Lys Ile
            515                 520                 525

Val Gly Pro Gly Lys Phe Gly Thr Asn Ala Glu Asp Gly Lys Ile Leu
            530                 535                 540

His Glu Met Gly Gly His Leu Ser Glu Val Leu Leu Ser Leu Val
545                 550                 555                 560

Val Leu Ser Asp Phe Ala Pro Glu Thr Ala Ser Val Met Tyr Leu Ile
                565                 570                 575

Leu His Phe Ser Ile Pro Gln Ser His Val Asp Val Met Asp Cys Asp
            580                 585                 590

Lys Thr Gln Leu Asn Leu Thr Val Glu Leu Thr Thr Ala Glu Val Ile
            595                 600                 605
```

-continued

```
Pro Gly Ser Val Trp Asn Leu Gly Lys Tyr Val Cys Ile Arg Pro Asn
    610                 615                 620

Trp Trp Pro Tyr Glu Thr Thr Val Val Leu Ala Phe Glu Glu Val Ser
625                 630                 635                 640

Gln Val Val Lys Leu Val Leu Arg Ala Leu Arg Asp Leu Thr Arg Ile
            645                 650                 655

Trp Asn Ala Ala Thr Thr Thr Ala Phe Leu Val Cys Leu Val Lys Ile
                660                 665                 670

Val Arg Gly Gln Met Val Gln Gly Ile Leu Trp Leu Leu Leu Ile Thr
        675                 680                 685

Gly Val Gln Gly His Leu Asp Cys Lys Pro Glu Phe Ser Tyr Ala Ile
    690                 695                 700

Ala Lys Asp Glu Arg Ile Gly Gln Leu Gly Ala Glu Gly Leu Thr Thr
705                 710                 715                 720

Thr Trp Lys Glu Tyr Ser Pro Gly Met Lys Leu Glu Asp Thr Met Val
            725                 730                 735

Ile Ala Trp Cys Glu Asp Gly Lys Leu Met Tyr Leu Gln Arg Cys Thr
                740                 745                 750

Arg Glu Thr Arg Tyr Leu Ala Ile Leu His Thr Arg Ala Leu Pro Thr
        755                 760                 765

Ser Val Val Phe Lys Lys Leu Phe Asp Gly Arg Lys Gln Glu Asp Val
    770                 775                 780

Val Glu Met Asn Asp Asn Phe Glu Phe Gly Leu Cys Pro Cys Asp Ala
785                 790                 795                 800

Lys Pro Ile Val Arg Gly Lys Phe Asn Thr Thr Leu Leu Asn Gly Pro
            805                 810                 815

Ala Phe Gln Met Val Cys Pro Ile Gly Trp Thr Gly Thr Val Ser Cys
                820                 825                 830

Thr Ser Phe Asn Met Asp Thr Leu Ala Thr Thr Val Arg Thr Tyr
        835                 840                 845

Arg Arg Ser Lys Pro Phe Pro His Arg Gln Gly Cys Ile Thr Gln Lys
    850                 855                 860

Asn Leu Gly Glu Asp Leu His Asn Cys Ile Leu Gly Asn Trp Thr
865                 870                 875                 880

Cys Val Pro Gly Asp Gln Leu Leu Tyr Lys Gly Gly Ser Ile Glu Ser
            885                 890                 895

Cys Lys Trp Cys Gly Tyr Gln Phe Lys Glu Ser Glu Gly Leu Pro His
                900                 905                 910

Tyr Pro Ile Gly Lys Cys Lys Leu Glu Asn Glu Thr Gly Tyr Arg Leu
        915                 920                 925

Val Asp Ser Thr Ser Cys Asn Arg Glu Gly Val Ala Ile Val Pro Gln
    930                 935                 940

Gly Thr Leu Lys Cys Lys Ile Gly Lys Thr Thr Val Gln Val Ile Ala
945                 950                 955                 960

Met Asp Thr Lys Leu Gly Pro Met Pro Cys Arg Pro Tyr Glu Ile Ile
            965                 970                 975

Ser Ser Glu Gly Pro Val Glu Lys Thr Ala Cys Thr Phe Asn Tyr Thr
                980                 985                 990

Lys Thr Leu Lys Asn Lys Tyr Phe Glu Pro Arg Asp Ser Tyr Phe Gln
        995                 1000                1005

Gln Tyr Met Leu Lys Gly Glu Tyr Gln Tyr Trp Phe Asp Leu Glu
    1010                1015                1020
```

-continued

| Val | Thr | Asp | His | His | Arg | Asp | Tyr | Phe | Ala | Glu | Ser | Ile | Leu | Val |
| | 1025 | | | | 1030 | | | | | 1035 | | | | |

Val Val Val Ala Leu Leu Gly Gly Arg Tyr Val Leu Trp Leu Leu
1040                    1045                    1050

Val Thr Tyr Met Val Leu Ser Glu Gln Lys Ala Leu Gly Ile Gln
1055                    1060                    1065

Tyr Gly Ser Gly Glu Val Val Met Met Gly Asn Leu Leu Thr His
1070                    1075                    1080

Asn Asn Ile Glu Val Val Thr Tyr Phe Leu Leu Leu Tyr Leu Leu
1085                    1090                    1095

Leu Arg Glu Glu Ser Val Lys Lys Trp Val Leu Leu Leu Tyr His
1100                    1105                    1110

Ile Leu Val Val His Pro Ile Lys Ser Val Ile Val Ile Leu Leu
1115                    1120                    1125

Met Ile Gly Asp Val Val Lys Ala Asp Ser Gly Gly Gln Glu Tyr
1130                    1135                    1140

Leu Gly Lys Ile Asp Leu Cys Phe Thr Thr Val Val Leu Ile Val
1145                    1150                    1155

Ile Gly Leu Ile Ile Ala Arg Arg Asp Pro Thr Ile Val Pro Leu
1160                    1165                    1170

Val Thr Ile Met Ala Ala Leu Arg Val Thr Glu Leu Thr His Gln
1175                    1180                    1185

Pro Gly Val Asp Ile Ala Val Ala Val Met Thr Ile Thr Leu Leu
1190                    1195                    1200

Met Val Ser Tyr Val Thr Asp Tyr Phe Arg Tyr Lys Lys Trp Leu
1205                    1210                    1215

Gln Cys Ile Leu Ser Leu Val Ser Ala Val Phe Leu Ile Arg Ser
1220                    1225                    1230

Leu Ile Tyr Leu Gly Arg Ile Glu Met Pro Glu Val Thr Ile Pro
1235                    1240                    1245

Asn Trp Arg Pro Leu Thr Leu Ile Leu Leu Tyr Leu Ile Ser Thr
1250                    1255                    1260

Thr Ile Val Thr Arg Trp Lys Val Asp Val Ala Gly Leu Leu Leu
1265                    1270                    1275

Gln Cys Val Pro Ile Leu Leu Leu Val Thr Thr Leu Trp Ala Asp
1280                    1285                    1290

Phe Leu Thr Leu Ile Leu Ile Leu Pro Thr Tyr Glu Leu Val Lys
1295                    1300                    1305

Leu Tyr Tyr Leu Lys Thr Val Arg Thr Asp Thr Glu Arg Ser Trp
1310                    1315                    1320

Leu Gly Gly Ile Asp Tyr Thr Arg Val Asp Ser Ile Tyr Asp Val
1325                    1330                    1335

Asp Glu Ser Gly Glu Gly Val Tyr Leu Phe Pro Ser Arg Gln Lys
1340                    1345                    1350

Ala Gln Gly Asn Phe Ser Ile Leu Leu Pro Leu Ile Lys Ala Thr
1355                    1360                    1365

Leu Ile Ser Cys Val Ser Ser Lys Trp Gln Leu Ile Tyr Met Ser
1370                    1375                    1380

Tyr Leu Thr Leu Asp Phe Met Tyr Tyr Met His Arg Lys Val Ile
1385                    1390                    1395

Glu Glu Ile Ser Gly Gly Thr Asn Ile Ile Ser Arg Leu Val Ala
1400                    1405                    1410

Ala Leu Ile Glu Leu Asn Trp Ser Met Glu Glu Glu Glu Ser Lys

-continued

```
                 1415                 1420                 1425
Gly Leu Lys Lys Phe Tyr Leu Leu Ser Gly Arg Leu Arg Asn Leu
        1430                1435                1440
Ile Ile Lys His Lys Val Arg Asn Glu Thr Val Ala Ser Trp Tyr
        1445                1450                1455
Gly Glu Glu Glu Val Tyr Gly Met Pro Lys Ile Met Thr Ile Ile
        1460                1465                1470
Lys Ala Ser Thr Leu Ser Lys Ser Arg His Cys Ile Ile Cys Thr
        1475                1480                1485
Val Cys Glu Gly Arg Glu Trp Lys Gly Gly Thr Cys Pro Lys Cys
        1490                1495                1500
Gly Arg His Gly Lys Pro Ile Thr Cys Gly Met Ser Leu Ala Asp
        1505                1510                1515
Phe Glu Glu Arg His Tyr Lys Arg Ile Phe Ile Arg Glu Gly Asn
        1520                1525                1530
Phe Glu Gly Met Cys Ser Arg Cys Gln Gly Lys His Arg Arg Phe
        1535                1540                1545
Glu Met Asp Arg Glu Pro Lys Ser Ala Arg Tyr Cys Ala Glu Cys
        1550                1555                1560
Asn Arg Leu His Pro Ala Glu Glu Gly Asp Phe Trp Ala Glu Ser
        1565                1570                1575
Ser Met Leu Gly Leu Lys Ile Thr Tyr Phe Ala Leu Met Asp Gly
        1580                1585                1590
Lys Val Tyr Asp Ile Thr Glu Trp Ala Gly Cys Gln Arg Val Gly
        1595                1600                1605
Ile Ser Pro Asp Thr His Arg Val Pro Cys His Ile Ser Phe Gly
        1610                1615                1620
Ser Arg Met Pro Phe Arg Gln Glu Tyr Asn Gly Phe Val Gln Tyr
        1625                1630                1635
Thr Ala Arg Gly Gln Leu Phe Leu Arg Asn Leu Pro Val Leu Ala
        1640                1645                1650
Thr Lys Val Lys Met Leu Met Val Gly Asn Leu Gly Glu Glu Ile
        1655                1660                1665
Gly Asn Leu Glu His Leu Gly Trp Ile Leu Arg Gly Pro Ala Val
        1670                1675                1680
Cys Lys Lys Ile Thr Glu His Glu Lys Cys His Ile Asn Ile Leu
        1685                1690                1695
Asp Lys Leu Thr Ala Phe Phe Gly Ile Met Pro Arg Gly Thr Thr
        1700                1705                1710
Pro Arg Ala Pro Val Arg Phe Pro Thr Ser Leu Leu Lys Val Arg
        1715                1720                1725
Arg Gly Leu Glu Thr Ala Trp Ala Tyr Thr His Gln Gly Gly Ile
        1730                1735                1740
Ser Ser Val Asp His Val Thr Ala Gly Lys Asp Leu Leu Val Cys
        1745                1750                1755
Asp Ser Met Gly Arg Thr Arg Val Val Cys Gln Ser Asn Asn Arg
        1760                1765                1770
Leu Thr Asp Glu Thr Glu Tyr Gly Val Lys Thr Asp Ser Gly Cys
        1775                1780                1785
Pro Asp Gly Ala Arg Cys Tyr Val Leu Asn Pro Glu Ala Val Asn
        1790                1795                1800
Ile Ser Gly Ser Lys Gly Ala Val Val His Leu Gln Lys Thr Gly
        1805                1810                1815
```

-continued

```
Gly Glu Phe Thr Cys Val Thr Ala Ser Gly Thr Pro Ala Phe Phe
    1820                1825                1830

Asp Leu Lys Asn Leu Lys Gly Trp Ser Gly Leu Pro Ile Phe Glu
    1835                1840                1845

Ala Ser Ser Gly Arg Val Val Gly Arg Val Lys Val Gly Lys Asn
    1850                1855                1860

Glu Glu Ser Lys Pro Thr Lys Ile Met Ser Gly Ile Gln Thr Val
    1865                1870                1875

Ser Lys Asn Arg Ala Asp Leu Thr Glu Met Val Lys Lys Ile Thr
    1880                1885                1890

Ser Met Asn Arg Gly Asp Phe Lys Gln Ile Thr Leu Ala Thr Gly
    1895                1900                1905

Ala Gly Lys Thr Thr Glu Leu Pro Lys Ala Val Ile Glu Glu Ile
    1910                1915                1920

Gly Arg His Lys Arg Val Leu Val Leu Ile Pro Leu Arg Ala Ala
    1925                1930                1935

Ala Glu Ser Val Tyr Gln Tyr Met Arg Leu Lys His Pro Ser Ile
    1940                1945                1950

Ser Phe Asn Leu Arg Ile Gly Asp Met Lys Glu Gly Asp Met Ala
    1955                1960                1965

Thr Gly Ile Thr Tyr Ala Ser Tyr Gly Tyr Phe Cys Gln Met Pro
    1970                1975                1980

Gln Pro Lys Leu Arg Ala Ala Met Val Glu Tyr Ser Tyr Ile Phe
    1985                1990                1995

Leu Asp Glu Tyr His Cys Ala Thr Pro Glu Gln Leu Ala Ile Ile
    2000                2005                2010

Gly Lys Ile His Arg Phe Ser Glu Ser Ile Arg Val Val Ala Met
    2015                2020                2025

Thr Ala Thr Pro Ala Gly Ser Val Thr Thr Thr Gly Gln Lys His
    2030                2035                2040

Pro Ile Glu Glu Phe Ile Ala Pro Glu Val Met Lys Gly Glu Asp
    2045                2050                2055

Leu Gly Ser Gln Phe Leu Asp Ile Ala Gly Leu Lys Ile Pro Val
    2060                2065                2070

Asp Glu Met Lys Gly Asn Met Leu Val Phe Val Pro Thr Arg Asn
    2075                2080                2085

Met Ala Val Glu Val Ala Lys Lys Leu Lys Ala Lys Gly Tyr Asn
    2090                2095                2100

Ser Gly Tyr Tyr Tyr Ser Gly Glu Asp Pro Ala Asn Leu Arg Val
    2105                2110                2115

Val Thr Ser Gln Ser Pro Tyr Val Ile Val Ala Thr Asn Ala Ile
    2120                2125                2130

Glu Ser Gly Val Thr Leu Pro Asp Leu Asp Thr Val Ile Asp Thr
    2135                2140                2145

Gly Leu Lys Cys Glu Lys Arg Val Arg Val Ser Ser Lys Ile Pro
    2150                2155                2160

Phe Ile Val Thr Gly Leu Lys Arg Met Ala Val Thr Val Gly Glu
    2165                2170                2175

Gln Ala Gln Arg Arg Gly Arg Val Gly Arg Val Lys Pro Gly Arg
    2180                2185                2190

Tyr Tyr Arg Ser Gln Glu Thr Ala Thr Gly Ser Lys Asp Tyr His
    2195                2200                2205
```

```
Tyr Asp Leu Leu Gln Ala Gln Arg Tyr Gly Ile Glu Asp Gly Ile
2210                2215                2220

Asn Val Thr Lys Ser Phe Arg Glu Met Asn Tyr Asp Trp Ser Leu
2225                2230                2235

Tyr Glu Glu Asp Ser Leu Leu Ile Thr Gln Leu Glu Ile Leu Asn
2240                2245                2250

Asn Leu Leu Ile Ser Glu Asp Leu Pro Ala Ala Val Lys Asn Ile
2255                2260                2265

Met Ala Arg Thr Asp His Pro Glu Pro Ile Gln Leu Ala Tyr Asn
2270                2275                2280

Ser Tyr Glu Val Gln Val Pro Val Leu Phe Pro Lys Ile Arg Asn
2285                2290                2295

Gly Glu Val Thr Asp Thr Tyr Glu Asn Tyr Ser Phe Leu Asn Ala
2300                2305                2310

Arg Lys Leu Gly Glu Asp Val Pro Val Tyr Ile Tyr Ala Thr Glu
2315                2320                2325

Asp Glu Asp Leu Ala Val Asp Leu Leu Gly Leu Asp Trp Pro Asp
2330                2335                2340

Pro Gly Asn Gln Gln Val Val Glu Thr Gly Lys Ala Leu Lys Gln
2345                2350                2355

Val Thr Gly Leu Ser Ser Ala Glu Asn Ala Leu Leu Val Ala Leu
2360                2365                2370

Phe Gly Tyr Val Gly Tyr Gln Ala Leu Ser Lys Arg His Val Pro
2375                2380                2385

Met Ile Thr Asp Ile Tyr Thr Ile Glu Asp Gln Arg Leu Glu Asp
2390                2395                2400

Thr Thr His Leu Gln Tyr Ala Pro Asn Ala Ile Lys Thr Asp Gly
2405                2410                2415

Thr Glu Thr Glu Leu Lys Glu Leu Ala Ser Gly Asp Val Glu Lys
2420                2425                2430

Ile Met Gly Ala Ile Ser Asp Tyr Ala Ala Gly Leu Glu Phe
2435                2440                2445

Val Lys Ser Gln Ala Glu Lys Ile Lys Thr Ala Pro Leu Phe Lys
2450                2455                2460

Glu Asn Ala Glu Ala Ala Lys Gly Tyr Val Gln Lys Phe Ile Asp
2465                2470                2475

Ser Leu Ile Glu Asn Lys Glu Glu Ile Ile Arg Tyr Gly Leu Trp
2480                2485                2490

Gly Thr His Thr Ala Leu Tyr Lys Ser Ile Ala Ala Arg Leu Gly
2495                2500                2505

His Glu Thr Ala Phe Ala Thr Leu Val Leu Lys Trp Leu Ala Phe
2510                2515                2520

Gly Gly Glu Ser Val Ser Asp His Val Lys Gln Ala Ala Val Asp
2525                2530                2535

Leu Val Val Tyr Tyr Val Met Asn Lys Pro Ser Phe Pro Gly Asp
2540                2545                2550

Ser Glu Thr Gln Gln Glu Gly Arg Arg Phe Val Ala Ser Leu Phe
2555                2560                2565

Ile Ser Ala Leu Ala Thr Tyr Thr Tyr Lys Thr Trp Asn Tyr His
2570                2575                2580

Asn Leu Ser Lys Val Val Glu Pro Ala Leu Ala Tyr Leu Pro Tyr
2585                2590                2595

Ala Thr Ser Ala Leu Lys Met Phe Thr Pro Thr Arg Leu Glu Ser
```

-continued

```
                    2600                2605                2610

Val Val Ile Leu Ser Thr Thr Ile Tyr Lys Thr Tyr Leu Ser Ile
        2615                2620                2625

Arg Lys Gly Lys Ser Asp Gly Leu Leu Gly Thr Gly Ile Ser Ala
        2630                2635                2640

Ala Met Glu Ile Leu Ser Gln Asn Pro Val Ser Val Gly Ile Ser
        2645                2650                2655

Val Met Leu Gly Val Gly Ala Ile Ala Ala His Asn Ala Ile Glu
        2660                2665                2670

Ser Ser Glu Gln Lys Arg Thr Leu Leu Met Lys Val Phe Val Lys
        2675                2680                2685

Asn Phe Leu Asp Gln Ala Ala Thr Asp Glu Leu Val Lys Glu Asn
        2690                2695                2700

Pro Glu Lys Ile Ile Met Ala Leu Phe Glu Ala Val Gln Thr Ile
        2705                2710                2715

Gly Asn Pro Leu Arg Leu Ile Tyr His Leu Tyr Gly Val Tyr Tyr
        2720                2725                2730

Lys Gly Trp Glu Ala Lys Glu Leu Ser Glu Arg Thr Ala Gly Arg
        2735                2740                2745

Asn Leu Phe Thr Leu Ile Met Phe Glu Ala Phe Glu Leu Leu Gly
        2750                2755                2760

Met Asp Ser Gln Gly Lys Ile Arg Asn Leu Ser Gly Asn Tyr Ile
        2765                2770                2775

Leu Asp Leu Ile Tyr Gly Leu His Lys Gln Ile Asn Arg Gly Leu
        2780                2785                2790

Lys Lys Met Val Leu Gly Trp Ala Pro Ala Pro Phe Ser Cys Asp
        2795                2800                2805

Trp Thr Pro Ser Asp Glu Arg Ile Arg Leu Pro Thr Asp Asn Tyr
        2810                2815                2820

Leu Arg Val Glu Thr Arg Cys Pro Cys Gly Tyr Glu Met Lys Ala
        2825                2830                2835

Phe Lys Asn Val Gly Gly Lys Leu Thr Lys Val Glu Glu Ser Gly
        2840                2845                2850

Pro Phe Leu Cys Arg Asn Arg Pro Gly Arg Gly Pro Val Asn Tyr
        2855                2860                2865

Arg Val Thr Lys Tyr Tyr Asp Asp Asn Leu Arg Glu Ile Lys Pro
        2870                2875                2880

Val Ala Lys Leu Glu Gly Gln Val Glu His Tyr Tyr Lys Gly Val
        2885                2890                2895

Thr Ala Lys Ile Asp Tyr Ser Lys Gly Lys Met Leu Leu Ala Thr
        2900                2905                2910

Asp Lys Trp Glu Val Glu His Gly Val Ile Thr Arg Leu Ala Lys
        2915                2920                2925

Arg Tyr Thr Gly Val Gly Phe Asn Gly Ala Tyr Leu Gly Asp Glu
        2930                2935                2940

Pro Asn His Arg Ala Leu Val Glu Arg Asp Cys Ala Thr Ile Thr
        2945                2950                2955

Lys Asn Thr Val Gln Phe Leu Lys Met Lys Lys Gly Cys Ala Phe
        2960                2965                2970

Thr Tyr Asp Leu Thr Ile Ser Asn Leu Thr Arg Leu Ile Glu Leu
        2975                2980                2985

Val His Arg Asn Asn Leu Glu Glu Lys Glu Ile Pro Thr Ala Thr
        2990                2995                3000
```

-continued

```
Val Thr Thr Trp Leu Ala Tyr Thr Phe Val Asn Glu Asp Val Gly
    3005                3010                3015

Thr Ile Lys Pro Val Leu Gly Glu Arg Val Ile Pro Asp Pro Val
    3020                3025                3030

Val Asp Ile Asn Leu Gln Pro Glu Val Gln Val Asp Thr Ser Glu
    3035                3040                3045

Val Gly Ile Thr Ile Ile Gly Arg Glu Thr Leu Met Thr Thr Gly
    3050                3055                3060

Val Thr Pro Val Leu Glu Lys Val Glu Pro Asp Ala Ser Asp Asn
    3065                3070                3075

Gln Asn Ser Val Lys Ile Gly Leu Asp Glu Gly Asn Tyr Pro Gly
    3080                3085                3090

Pro Gly Ile Gln Thr His Thr Leu Thr Glu Glu Ile His Asn Arg
    3095                3100                3105

Asp Ala Arg Pro Phe Ile Met Ile Leu Gly Ser Arg Asn Ser Ile
    3110                3115                3120

Ser Asn Arg Ala Lys Thr Ala Arg Asn Ile Asn Leu Tyr Thr Gly
    3125                3130                3135

Asn Asp Pro Arg Glu Ile Arg Asp Leu Met Ala Ala Gly Arg Met
    3140                3145                3150

Leu Val Val Ala Leu Arg Asp Val Asp Pro Glu Leu Ser Glu Met
    3155                3160                3165

Val Asp Phe Lys Gly Thr Phe Leu Asp Arg Glu Ala Leu Glu Ala
    3170                3175                3180

Leu Ser Leu Gly Gln Pro Lys Pro Lys Gln Val Thr Lys Glu Ala
    3185                3190                3195

Val Arg Asn Leu Ile Glu Gln Lys Lys Asp Val Glu Ile Pro Asn
    3200                3205                3210

Trp Phe Ala Ser Asp Asp Pro Val Phe Leu Glu Val Ala Leu Lys
    3215                3220                3225

Asn Asp Lys Tyr Tyr Leu Val Gly Asp Val Gly Glu Leu Lys Asp
    3230                3235                3240

Gln Ala Lys Ala Leu Gly Ala Thr Asp Gln Thr Arg Ile Ile Lys
    3245                3250                3255

Glu Val Gly Ser Arg Thr Tyr Ala Met Lys Leu Ser Ser Trp Phe
    3260                3265                3270

Leu Lys Ala Ser Asn Lys Gln Met Ser Leu Thr Pro Leu Phe Glu
    3275                3280                3285

Glu Leu Leu Leu Arg Cys Pro Pro Ala Thr Lys Ser Asn Lys Gly
    3290                3295                3300

His Met Ala Ser Ala Tyr Gln Leu Ala Gln Gly Asn Trp Glu Pro
    3305                3310                3315

Leu Gly Cys Gly Val His Leu Gly Thr Ile Pro Ala Arg Arg Val
    3320                3325                3330

Lys Ile His Pro Tyr Glu Ala Tyr Leu Lys Leu Lys Asp Phe Ile
    3335                3340                3345

Glu Glu Glu Glu Lys Lys Pro Arg Val Lys Asp Thr Val Ile Arg
    3350                3355                3360

Glu His Asn Lys Trp Ile Leu Lys Lys Ile Arg Phe Gln Gly Asn
    3365                3370                3375

Leu Asn Thr Lys Lys Met Leu Asn Pro Gly Lys Leu Ser Glu Gln
    3380                3385                3390
```

-continued

```
Leu Asp Arg Glu Gly Arg Lys Arg Asn Ile Tyr Asn His Gln Ile
3395                3400                3405

Gly Thr Ile Met Ser Ser Ala Gly Ile Arg Leu Glu Lys Leu Pro
3410                3415                3420

Ile Val Arg Ala Gln Thr Asp Thr Lys Thr Phe His Glu Ala Ile
3425                3430                3435

Arg Asp Lys Ile Asp Lys Ser Glu Asn Arg Gln Asn Pro Glu Leu
3440                3445                3450

His Asn Lys Leu Leu Glu Ile Phe His Thr Ile Ala Gln Pro Thr
3455                3460                3465

Leu Lys His Thr Tyr Gly Glu Val Thr Trp Glu Gln Leu Glu Ala
3470                3475                3480

Gly Val Asn Arg Lys Gly Ala Ala Gly Phe Leu Glu Lys Lys Asn
3485                3490                3495

Ile Gly Glu Val Leu Asp Ser Glu Lys His Leu Val Glu Gln Leu
3500                3505                3510

Val Arg Asp Leu Lys Ala Gly Arg Lys Ile Lys Tyr Tyr Glu Thr
3515                3520                3525

Ala Ile Pro Lys Asn Glu Lys Arg Asp Val Ser Asp Asp Trp Gln
3530                3535                3540

Ala Gly Asp Leu Val Val Glu Lys Arg Pro Arg Val Ile Gln Tyr
3545                3550                3555

Pro Glu Ala Lys Thr Arg Leu Ala Ile Thr Lys Val Met Tyr Asn
3560                3565                3570

Trp Val Lys Gln Gln Pro Val Val Ile Pro Gly Tyr Glu Gly Lys
3575                3580                3585

Thr Pro Leu Phe Asn Ile Phe Asp Lys Val Arg Lys Glu Trp Asp
3590                3595                3600

Ser Phe Asn Glu Pro Val Ala Val Ser Phe Asp Thr Lys Ala Trp
3605                3610                3615

Asp Thr Gln Val Thr Ser Lys Asp Leu Gln Leu Ile Gly Glu Ile
3620                3625                3630

Gln Lys Tyr Tyr Tyr Lys Lys Glu Trp His Lys Phe Ile Asp Thr
3635                3640                3645

Ile Thr Asp His Met Thr Glu Val Pro Val Ile Thr Ala Asp Gly
3650                3655                3660

Glu Val Tyr Ile Arg Asn Gly Gln Arg Gly Ser Gly Gln Pro Asp
3665                3670                3675

Thr Ser Ala Gly Asn Ser Met Leu Asn Val Leu Thr Met Met Tyr
3680                3685                3690

Gly Phe Cys Glu Ser Thr Gly Val Pro Tyr Lys Ser Phe Asn Arg
3695                3700                3705

Val Ala Arg Ile His Val Cys Gly Asp Asp Gly Phe Leu Ile Thr
3710                3715                3720

Glu Lys Gly Leu Gly Leu Lys Phe Ala Asn Lys Gly Met Gln Ile
3725                3730                3735

Leu His Glu Ala Gly Lys Pro Gln Lys Ile Thr Glu Gly Glu Lys
3740                3745                3750

Met Lys Val Ala Tyr Arg Phe Glu Asp Ile Glu Phe Cys Ser His
3755                3760                3765

Thr Pro Val Pro Val Arg Trp Ser Asp Asn Thr Ser Ser His Met
3770                3775                3780

Ala Gly Arg Asp Thr Ala Val Ile Leu Ser Lys Met Ala Thr Arg
```

-continued

```
             3785                3790                3795

Leu Asp Ser Ser Gly Glu Arg Gly Thr Thr Ala Tyr Glu Lys Ala
    3800                3805                3810

Val Ala Phe Ser Phe Leu Leu Met Tyr Ser Trp Asn Pro Leu Val
    3815                3820                3825

Arg Arg Ile Cys Leu Leu Val Leu Ser Gln Gln Pro Glu Thr Asp
    3830                3835                3840

Pro Ser Lys His Ala Thr Tyr Tyr Lys Gly Asp Pro Ile Gly
    3845                3850                3855

Ala Tyr Lys Asp Val Ile Gly Arg Asn Leu Ser Glu Leu Lys Arg
    3860                3865                3870

Thr Gly Phe Glu Lys Leu Ala Asn Leu Asn Leu Ser Leu Ser Thr
    3875                3880                3885

Leu Gly Val Trp Thr Lys His Thr Ser Lys Arg Ile Ile Gln Asp
    3890                3895                3900

Cys Val Ala Ile Gly Lys Glu Gly Asn Trp Leu Val Lys Pro
    3905                3910                3915

Asp Arg Leu Ile Ser Ser Lys Thr Gly His Leu Tyr Ile Pro Asp
    3920                3925                3930

Lys Gly Phe Thr Leu Gln Gly Lys His Tyr Glu Gln Leu Gln Leu
    3935                3940                3945

Arg Thr Glu Thr Asn Pro Val Met Gly Val Gly Thr Glu Arg Tyr
    3950                3955                3960

Lys Leu Gly Pro Ile Val Asn Leu Leu Leu Arg Arg Leu Lys Ile
    3965                3970                3975

Leu Leu Met Thr Ala Val Gly Val Ser Ser
    3980                3985

<210> SEQ ID NO 6
<211> LENGTH: 3898
<212> TYPE: PRT
<213> ORGANISM: Pestivirus bovine viral diarrhea virus 1

<400> SEQUENCE: 6

Met Glu Leu Ile Thr Asn Glu Leu Leu Tyr Lys Thr Tyr Lys Gln Lys
1               5                   10                  15

Pro Val Gly Val Glu Glu Pro Val Tyr Asp Gln Ala Gly Asn Pro Leu
                20                  25                  30

Phe Gly Glu Arg Gly Ala Ile His Pro Gln Ser Thr Leu Lys Leu Pro
            35                  40                  45

His Lys Arg Gly Glu Arg Asn Val Pro Thr Ser Leu Ala Ser Leu Pro
        50                  55                  60

Lys Arg Gly Asp Cys Arg Ser Gly Asn Ser Lys Gly Pro Val Ser Gly
65                  70                  75                  80

Ile Tyr Leu Lys Pro Gly Pro Leu Phe Tyr Gln Asp Tyr Lys Gly Pro
                85                  90                  95

Val Tyr His Arg Ala Pro Leu Glu Leu Phe Glu Glu Gly Ser Met Cys
            100                 105                 110

Glu Thr Thr Lys Arg Ile Gly Arg Val Thr Gly Ser Asp Gly Lys Leu
        115                 120                 125

Tyr His Ile Tyr Ile Cys Ile Asp Gly Cys Ile Thr Val Lys Ser Ala
    130                 135                 140

Thr Arg Ser His Gln Arg Val Leu Arg Trp Val His Asn Arg Leu Asp
145                 150                 155                 160
```

-continued

```
Cys Pro Leu Trp Val Thr Ser Cys Ser Asp Thr Lys Glu Glu Gly Ala
            165                 170                 175
Thr Lys Lys Gln Gln Lys Pro Asp Arg Leu Glu Lys Gly Arg Met
        180                 185                 190
Lys Ile Val Pro Lys Glu Ser Glu Lys Asp Ser Lys Thr Lys Pro Pro
            195                 200                 205
Asp Ala Thr Ile Val Val Asp Gly Val Lys Tyr Gln Val Lys Lys Lys
210                 215                 220
Gly Lys Val Lys Ser Lys Asn Thr Gln Asp Gly Leu Tyr His Asn Lys
225                 230                 235                 240
Asn Lys Pro Pro Glu Ser Arg Lys Lys Leu Glu Lys Ala Leu Leu Ala
                245                 250                 255
Trp Ala Ile Leu Ala Val Val Leu Ile Glu Val Thr Met Gly Glu Asn
                260                 265                 270
Ile Thr Gln Trp Asn Leu Gln Asp Asn Gly Thr Glu Gly Ile Gln Arg
            275                 280                 285
Ala Met Phe Gln Arg Gly Val Asn Arg Ser Leu His Gly Ile Trp Pro
        290                 295                 300
Glu Lys Ile Cys Thr Gly Val Pro Ser His Leu Ala Thr Asp Val Glu
305                 310                 315                 320
Leu Lys Thr Ile His Gly Met Met Asp Ala Ser Glu Lys Thr Asn Tyr
                325                 330                 335
Thr Cys Cys Arg Leu Gln Arg His Glu Trp Asn Lys His Gly Trp Cys
                340                 345                 350
Asn Trp Tyr Asn Ile Glu Pro Trp Ile Leu Ile Met Asn Arg Thr Gln
            355                 360                 365
Ala Asn Leu Thr Glu Gly Gln Pro Pro Arg Glu Cys Ala Val Thr Cys
        370                 375                 380
Arg Tyr Asp Arg Asp Ser Asp Leu Asn Val Val Thr Gln Ala Arg Asp
385                 390                 395                 400
Ser Pro Thr Pro Leu Thr Gly Cys Lys Lys Gly Lys Asn Phe Ser Phe
                405                 410                 415
Ala Gly Val Leu Thr Arg Gly Pro Cys Asn Phe Glu Ile Ala Ala Ser
                420                 425                 430
Asp Val Leu Phe Lys Glu His Glu Cys Thr Gly Val Phe Gln Asp Thr
            435                 440                 445
Ala His Tyr Leu Val Asp Gly Val Thr Asn Ser Leu Glu Ser Ala Arg
        450                 455                 460
Gln Gly Thr Ala Lys Leu Thr Thr Trp Leu Gly Lys Gln Leu Gly Ile
465                 470                 475                 480
Leu Gly Lys Lys Leu Glu Asn Lys Ser Lys Thr Trp Phe Gly Ala Tyr
                485                 490                 495
Ala Ala Ser Pro Tyr Cys Asp Val Asp Arg Lys Ile Gly Tyr Ile Trp
                500                 505                 510
Phe Thr Lys Asn Cys Thr Pro Ala Cys Leu Pro Lys Asn Thr Lys Ile
            515                 520                 525
Ile Gly Pro Gly Lys Phe Asp Thr Asn Ala Glu Asp Gly Lys Ile Leu
        530                 535                 540
His Glu Met Gly Gly His Leu Ser Glu Val Leu Leu Leu Ser Leu Val
545                 550                 555                 560
Val Leu Ser Asp Phe Ala Pro Glu Thr Ala Ser Ala Met Tyr Leu Ile
                565                 570                 575
Leu His Phe Ser Ile Pro Gln Ser His Val Asp Ile Thr Asp Cys Asp
```

-continued

```
                580                 585                 590
Lys Thr Gln Leu Asn Leu Thr Ile Glu Leu Thr Thr Ala Asp Val Ile
        595                 600                 605
Pro Gly Ser Val Trp Asn Leu Gly Lys Tyr Val Cys Ile Arg Pro Asp
        610                 615                 620
Trp Trp Pro Tyr Glu Thr Ala Val Leu Ala Phe Glu Glu Val Gly
625                 630                 635                 640
Gln Val Val Lys Ile Val Leu Arg Ala Leu Arg Asp Leu Thr Arg Ile
                645                 650                 655
Trp Asn Ala Ala Thr Thr Ala Phe Leu Val Cys Leu Ile Lys Met
                660                 665                 670
Val Arg Gly Gln Val Val Gln Gly Ile Leu Trp Leu Leu Ile Thr
        675                 680                 685
Gly Val Gln Gly His Leu Asp Cys Lys Pro Glu Tyr Ser Tyr Ala Ile
        690                 695                 700
Ala Lys Asn Asp Arg Val Gly Pro Leu Gly Ala Glu Gly Leu Thr Thr
705                 710                 715                 720
Val Trp Lys Asp Tyr Ser His Glu Met Lys Leu Glu Asp Thr Met Val
                725                 730                 735
Ile Ala Trp Cys Lys Gly Gly Lys Phe Thr Tyr Leu Ser Arg Cys Thr
                740                 745                 750
Arg Glu Thr Arg Tyr Leu Ala Ile Leu His Ser Arg Ala Leu Pro Thr
        755                 760                 765
Ser Val Val Phe Lys Lys Leu Phe Glu Gly Gln Lys Gln Glu Asp Thr
        770                 775                 780
Val Glu Met Asp Asp Asp Phe Glu Phe Gly Leu Cys Pro Cys Asp Ala
785                 790                 795                 800
Lys Pro Ile Val Arg Gly Lys Phe Asn Thr Thr Leu Leu Asn Gly Pro
                805                 810                 815
Ala Phe Gln Met Val Cys Pro Ile Gly Trp Thr Gly Thr Val Ser Cys
                820                 825                 830
Met Leu Ala Asn Arg Asp Thr Leu Asp Thr Ala Val Val Arg Thr Tyr
        835                 840                 845
Arg Arg Ser Val Pro Phe Pro Tyr Arg Gln Gly Cys Ile Thr Gln Lys
        850                 855                 860
Thr Leu Gly Glu Asp Leu Tyr Asp Cys Ala Leu Gly Gly Asn Trp Thr
865                 870                 875                 880
Cys Val Thr Gly Asp Gln Ser Arg Tyr Thr Gly Gly Leu Ile Glu Ser
                885                 890                 895
Cys Lys Trp Cys Gly Tyr Lys Phe Gln Lys Ser Glu Gly Leu Pro His
                900                 905                 910
Tyr Pro Ile Gly Lys Cys Arg Leu Asn Asn Glu Thr Gly Tyr Arg Leu
        915                 920                 925
Val Asp Asp Thr Ser Cys Asp Arg Glu Gly Val Ala Ile Val Pro His
        930                 935                 940
Gly Leu Val Lys Cys Lys Ile Gly Asp Thr Thr Val Gln Val Ile Ala
945                 950                 955                 960
Thr Asp Thr Lys Leu Gly Pro Met Pro Cys Lys Pro His Glu Ile Ile
                965                 970                 975
Ser Ser Glu Gly Pro Ile Glu Lys Thr Ala Cys Thr Phe Asn Tyr Thr
        980                 985                 990
Arg Thr Leu Lys Asn Lys Tyr Phe Glu Pro Arg Asp Ser Tyr Phe Gln
        995                 1000                1005
```

-continued

```
Gln Tyr Met Leu Lys Gly Asp Tyr Gln Tyr Trp Phe Asp Leu Glu
    1010                1015                1020

Val Thr Asp His His Arg Asp Tyr Phe Ala Glu Ser Ile Leu Val
    1025                1030                1035

Val Val Val Ala Leu Leu Gly Gly Arg Tyr Val Leu Trp Leu Leu
    1040                1045                1050

Val Thr Tyr Met Val Leu Ser Glu Gln Lys Ala Ser Gly Ala Gln
    1055                1060                1065

Tyr Gly Ala Gly Glu Val Val Met Met Gly Asn Leu Leu Thr His
    1070                1075                1080

Asp Asn Val Glu Val Val Thr Tyr Phe Phe Leu Leu Tyr Leu Leu
    1085                1090                1095

Leu Arg Glu Glu Ser Val Lys Lys Trp Val Leu Leu Leu Tyr His
    1100                1105                1110

Ile Leu Val Ala His Pro Leu Lys Ser Val Ile Val Ile Leu Leu
    1115                1120                1125

Met Ile Gly Asp Val Val Lys Ala Asp Pro Gly Gly Gln Gly Tyr
    1130                1135                1140

Leu Gly Gln Ile Asp Val Cys Phe Thr Met Val Val Ile Ile Ile
    1145                1150                1155

Ile Gly Leu Ile Ile Ala Arg Arg Asp Pro Thr Ile Val Pro Leu
    1160                1165                1170

Ile Thr Ile Val Ala Ser Leu Arg Val Thr Gly Leu Thr Tyr Ser
    1175                1180                1185

Pro Gly Val Asp Ala Ala Met Ala Val Ile Thr Ile Thr Leu Leu
    1190                1195                1200

Met Val Ser Tyr Val Thr Asp Tyr Phe Arg Tyr Lys Arg Trp Leu
    1205                1210                1215

Gln Cys Ile Leu Ser Leu Val Ser Gly Val Phe Leu Ile Arg Cys
    1220                1225                1230

Leu Ile His Leu Gly Arg Ile Glu Thr Pro Glu Val Thr Ile Pro
    1235                1240                1245

Asn Trp Arg Pro Leu Thr Leu Ile Leu Phe Tyr Leu Ile Ser Thr
    1250                1255                1260

Thr Val Val Thr Met Trp Lys Ile Asp Leu Ala Gly Leu Leu Leu
    1265                1270                1275

Gln Gly Val Pro Ile Leu Leu Leu Ile Thr Thr Leu Trp Ala Asp
    1280                1285                1290

Phe Leu Thr Leu Ile Leu Ile Leu Pro Thr Tyr Glu Leu Val Lys
    1295                1300                1305

Leu Tyr Tyr Leu Lys Thr Ile Lys Thr Asp Ile Glu Lys Ser Trp
    1310                1315                1320

Leu Gly Gly Leu Asp Tyr Lys Arg Val Asp Ser Ile Tyr Asp Val
    1325                1330                1335

Asp Glu Ser Gly Glu Gly Val Tyr Leu Phe Pro Ser Arg Gln Lys
    1340                1345                1350

Ala Gln Lys Asn Phe Ser Met Leu Leu Pro Leu Val Arg Ala Thr
    1355                1360                1365

Leu Ile Ser Cys Val Ser Ser Lys Trp Gln Leu Ile Tyr Met Ala
    1370                1375                1380

Tyr Leu Ser Val Asp Phe Met Tyr Tyr Met His Arg Lys Val Ile
    1385                1390                1395
```

-continued

| | | | | | | | | | | | |
|---|---|---|---|---|---|---|---|---|---|---|---|
|Glu|Glu|Ile|Ser|Gly|Gly|Thr|Asn|Met|Ile|Ser|Arg|Ile|Val|Ala|
| |1400| | | | |1405| | | |1410| | | | |

Ala Leu Ile Glu Leu Asn Trp Ser Met Glu Glu Glu Glu Ser Lys
    1415                1420                1425

Gly Leu Lys Lys Phe Tyr Leu Leu Ser Gly Arg Leu Arg Asn Leu
    1430                1435                1440

Ile Ile Lys His Lys Val Arg Asn Glu Thr Val Ala Gly Trp Tyr
    1445                1450                1455

Gly Glu Glu Glu Val Tyr Gly Met Pro Lys Ile Met Thr Ile Ile
    1460                1465                1470

Lys Ala Ser Thr Leu Asn Lys Asn Lys His Cys Ile Ile Cys Thr
    1475                1480                1485

Val Cys Glu Gly Arg Lys Trp Lys Gly Gly Thr Cys Pro Lys Cys
    1490                1495                1500

Gly Arg His Gly Lys Pro Ile Thr Cys Gly Met Ser Leu Ala Asp
    1505                1510                1515

Phe Glu Glu Arg His Tyr Lys Arg Ile Phe Ile Arg Glu Gly Asn
    1520                1525                1530

Phe Glu Gly Pro Phe Arg Gln Glu Tyr Asn Gly Phe Ile Gln Tyr
    1535                1540                1545

Thr Ala Arg Gly Gln Leu Phe Leu Arg Asn Leu Pro Ile Leu Ala
    1550                1555                1560

Thr Lys Val Lys Met Leu Met Val Gly Asn Leu Gly Glu Glu Val
    1565                1570                1575

Gly Asp Leu Glu His Leu Gly Trp Ile Leu Arg Gly Pro Ala Val
    1580                1585                1590

Cys Lys Lys Ile Thr Glu His Glu Arg Cys His Ile Asn Ile Leu
    1595                1600                1605

Asp Lys Leu Thr Ala Phe Phe Gly Ile Met Pro Arg Gly Thr Thr
    1610                1615                1620

Pro Arg Ala Pro Val Arg Phe Pro Thr Ser Leu Leu Lys Val Arg
    1625                1630                1635

Arg Gly Leu Glu Thr Gly Trp Ala Tyr Thr His Gln Gly Gly Ile
    1640                1645                1650

Ser Ser Val Asp His Val Thr Ala Gly Lys Asp Leu Leu Val Cys
    1655                1660                1665

Asp Ser Met Gly Arg Thr Arg Val Val Cys Gln Ser Asn Asn Lys
    1670                1675                1680

Leu Thr Asp Glu Thr Glu Tyr Gly Val Lys Thr Asp Ser Gly Cys
    1685                1690                1695

Pro Asp Gly Ala Arg Cys Tyr Val Leu Asn Pro Glu Ala Val Asn
    1700                1705                1710

Ile Ser Gly Ser Lys Gly Ala Val Val His Leu Gln Lys Thr Gly
    1715                1720                1725

Gly Glu Phe Thr Cys Val Thr Ala Ser Gly Thr Pro Ala Phe Phe
    1730                1735                1740

Asp Leu Lys Asn Leu Lys Gly Trp Ser Gly Leu Pro Ile Phe Glu
    1745                1750                1755

Ala Ser Ser Gly Arg Val Val Gly Arg Val Lys Val Gly Lys Asn
    1760                1765                1770

Glu Glu Ser Lys Pro Thr Lys Ile Met Ser Gly Ile Gln Thr Val
    1775                1780                1785

Ser Lys Asn Thr Ala Asp Leu Thr Glu Met Val Lys Lys Ile Thr

-continued

```
            1790                1795                1800
Ser Met Asn Arg Gly Asp Phe Lys Gln Ile Thr Leu Ala Thr Gly
    1805                1810                1815

Ala Gly Lys Thr Thr Glu Leu Pro Lys Ala Val Ile Glu Glu Ile
    1820                1825                1830

Gly Arg His Lys Arg Val Leu Val Leu Ile Pro Leu Arg Ala Ala
    1835                1840                1845

Ala Glu Ser Val Tyr Gln Tyr Met Arg Leu Lys His Pro Ser Ile
    1850                1855                1860

Ser Phe Asn Leu Arg Ile Gly Asp Met Lys Glu Gly Asp Met Ala
    1865                1870                1875

Thr Gly Ile Thr Tyr Ala Ser Tyr Gly Tyr Phe Cys Gln Met Pro
    1880                1885                1890

Gln Pro Lys Leu Arg Ala Ala Met Val Glu Tyr Ser Tyr Ile Phe
    1895                1900                1905

Leu Asp Glu Tyr His Cys Ala Thr Pro Glu Gln Leu Ala Ile Ile
    1910                1915                1920

Gly Lys Ile His Arg Phe Ser Glu Ser Ile Arg Val Val Ala Met
    1925                1930                1935

Thr Ala Thr Pro Ala Gly Ser Val Thr Thr Thr Gly Gln Lys His
    1940                1945                1950

Pro Ile Glu Glu Phe Ile Ala Pro Glu Val Met Glu Gly Glu Asp
    1955                1960                1965

Leu Gly Ser Gln Phe Leu Asp Ile Ala Gly Leu Lys Ile Pro Val
    1970                1975                1980

Asp Glu Met Lys Gly Asn Met Leu Val Phe Val Pro Thr Arg Asn
    1985                1990                1995

Met Ala Val Glu Val Ala Lys Lys Leu Lys Ala Lys Gly Tyr Asn
    2000                2005                2010

Ser Gly Tyr Tyr Tyr Ser Gly Glu Asp Pro Ala Asn Leu Arg Val
    2015                2020                2025

Val Thr Ser Gln Ser Pro Tyr Val Ile Val Ala Thr Asn Ala Ile
    2030                2035                2040

Glu Ser Gly Val Thr Leu Pro Asp Leu Asp Thr Val Val Asp Thr
    2045                2050                2055

Gly Leu Lys Cys Glu Lys Arg Val Arg Val Ser Ser Lys Ile Pro
    2060                2065                2070

Phe Ile Val Thr Gly Leu Lys Arg Met Ala Val Thr Val Gly Glu
    2075                2080                2085

Gln Ala Gln Arg Arg Gly Arg Val Gly Arg Val Lys Pro Gly Arg
    2090                2095                2100

Tyr Tyr Arg Ser Gln Glu Thr Ala Thr Gly Ser Lys Asp Tyr His
    2105                2110                2115

Tyr Asp Leu Leu Gln Ala Gln Arg Tyr Gly Ile Glu Asp Gly Ile
    2120                2125                2130

Asn Val Thr Lys Ser Phe Arg Glu Met Asn Tyr Asp Trp Ser Leu
    2135                2140                2145

Tyr Glu Glu Asp Ser Leu Leu Ile Thr Gln Leu Glu Ile Leu Asn
    2150                2155                2160

Asn Leu Leu Ile Ser Glu Asp Leu Pro Ala Ala Val Lys Asn Ile
    2165                2170                2175

Met Ala Arg Thr Asp His Pro Glu Pro Ile Gln Leu Ala Tyr Asn
    2180                2185                2190
```

-continued

```
Ser Tyr Glu Val Gln Val Pro Val Leu Phe Pro Lys Ile Arg Asn
    2195                2200                2205

Gly Glu Val Thr Asp Thr Tyr Glu Asn Tyr Ser Phe Leu Asn Ala
    2210                2215                2220

Arg Lys Leu Gly Glu Asp Val Pro Val Tyr Ile Tyr Ala Thr Glu
    2225                2230                2235

Asp Glu Asp Leu Ala Val Asp Leu Leu Gly Leu Asp Trp Pro Asp
    2240                2245                2250

Pro Gly Asn Gln Gln Val Val Glu Thr Gly Lys Ala Leu Lys Gln
    2255                2260                2265

Val Ala Gly Leu Ser Ser Ala Glu Asn Ala Leu Leu Val Ala Leu
    2270                2275                2280

Phe Gly Tyr Val Gly Tyr Gln Ala Leu Ser Lys Arg His Val Pro
    2285                2290                2295

Met Ile Thr Asp Ile Tyr Thr Ile Glu Asp Gln Arg Leu Glu Asp
    2300                2305                2310

Thr Thr His Leu Gln Tyr Ala Pro Asn Ala Ile Lys Thr Glu Gly
    2315                2320                2325

Thr Glu Thr Glu Leu Lys Glu Leu Ala Ser Gly Asp Val Glu Lys
    2330                2335                2340

Ile Met Gly Ala Ile Ser Asp Tyr Ala Ala Gly Gly Leu Asp Phe
    2345                2350                2355

Val Lys Ser Gln Ala Glu Lys Ile Lys Thr Ala Pro Leu Phe Lys
    2360                2365                2370

Glu Asn Val Glu Ala Ala Arg Gly Tyr Val Gln Lys Leu Ile Asp
    2375                2380                2385

Ser Leu Ile Glu Asp Lys Asp Val Ile Ile Arg Tyr Gly Leu Trp
    2390                2395                2400

Gly Thr His Thr Ala Leu Tyr Lys Ser Ile Ala Ala Arg Leu Gly
    2405                2410                2415

His Glu Thr Ala Phe Ala Thr Leu Val Leu Lys Trp Leu Ala Phe
    2420                2425                2430

Gly Gly Glu Thr Val Ser Asp His Ile Arg Gln Ala Ala Val Asp
    2435                2440                2445

Leu Val Val Tyr Tyr Val Met Asn Lys Pro Ser Phe Pro Gly Asp
    2450                2455                2460

Thr Glu Thr Gln Gln Glu Gly Arg Arg Phe Val Ala Ser Leu Phe
    2465                2470                2475

Ile Ser Ala Leu Ala Thr Tyr Thr Tyr Lys Thr Trp Asn Tyr Asn
    2480                2485                2490

Asn Leu Ser Lys Val Val Glu Pro Ala Leu Ala Tyr Leu Pro Tyr
    2495                2500                2505

Ala Thr Ser Ala Leu Lys Met Phe Thr Pro Thr Arg Leu Glu Ser
    2510                2515                2520

Val Val Ile Leu Ser Thr Ile Tyr Lys Thr Tyr Leu Ser Ile
    2525                2530                2535

Arg Lys Gly Lys Ser Asp Gly Leu Leu Gly Thr Gly Ile Ser Ala
    2540                2545                2550

Ala Met Glu Ile Leu Ser Gln Asn Pro Val Ser Val Gly Ile Ser
    2555                2560                2565

Val Met Leu Gly Val Gly Ala Ile Ala Ala His Asn Ala Ile Glu
    2570                2575                2580
```

-continued

Ser Ser Glu Gln Lys Arg Thr Leu Leu Met Lys Val Phe Val Lys
2585                 2590                2595

Asn Phe Leu Asp Gln Ala Ala Thr Asp Glu Leu Val Lys Glu Asn
2600                 2605                2610

Pro Glu Lys Ile Ile Met Ala Leu Phe Glu Ala Val Gln Thr Ile
2615                 2620                2625

Gly Asn Pro Leu Arg Leu Ile Tyr His Leu Tyr Gly Val Tyr Tyr
2630                 2635                2640

Lys Gly Trp Glu Ala Lys Glu Leu Ser Glu Arg Thr Ala Gly Arg
2645                 2650                2655

Asn Leu Phe Thr Leu Ile Met Phe Glu Ala Phe Glu Leu Leu Gly
2660                 2665                2670

Met Asp Ser Glu Gly Lys Ile Arg Asn Leu Ser Gly Asn Tyr Ile
2675                 2680                2685

Leu Asp Leu Ile His Gly Leu His Lys Gln Ile Asn Arg Gly Leu
2690                 2695                2700

Lys Lys Ile Val Leu Gly Trp Ala Pro Ala Pro Phe Ser Cys Asp
2705                 2710                2715

Trp Thr Pro Ser Asp Glu Arg Ile Arg Leu Pro Thr Asp Ser Tyr
2720                 2725                2730

Leu Arg Val Glu Thr Lys Cys Pro Cys Gly Tyr Glu Met Lys Ala
2735                 2740                2745

Leu Lys Asn Val Ser Gly Lys Leu Thr Lys Val Glu Glu Ser Gly
2750                 2755                2760

Pro Phe Leu Cys Arg Asn Arg Pro Gly Arg Gly Pro Val Asn Tyr
2765                 2770                2775

Arg Val Thr Lys Tyr Tyr Asp Asp Asn Leu Arg Glu Ile Arg Pro
2780                 2785                2790

Val Ala Lys Leu Glu Gly Gln Val Glu His Tyr Tyr Lys Gly Val
2795                 2800                2805

Thr Ala Arg Ile Asp Tyr Ser Lys Gly Lys Thr Leu Leu Ala Thr
2810                 2815                2820

Asp Lys Trp Glu Val Glu His Gly Thr Leu Thr Arg Leu Thr Lys
2825                 2830                2835

Arg Tyr Thr Gly Val Gly Phe Arg Gly Ala Tyr Leu Gly Asp Glu
2840                 2845                2850

Pro Asn His Arg Asp Leu Val Glu Arg Asp Cys Ala Thr Ile Thr
2855                 2860                2865

Lys Asn Thr Val Gln Phe Leu Lys Met Lys Lys Gly Cys Ala Phe
2870                 2875                2880

Thr Tyr Asp Leu Thr Ile Ser Asn Leu Thr Arg Leu Ile Glu Leu
2885                 2890                2895

Val His Arg Asn Asn Leu Glu Glu Lys Glu Ile Pro Thr Ala Thr
2900                 2905                2910

Val Thr Thr Trp Leu Ala Tyr Thr Phe Val Asn Glu Asp Val Gly
2915                 2920                2925

Thr Ile Lys Pro Val Leu Gly Glu Arg Val Ile Pro Asp Pro Val
2930                 2935                2940

Val Asp Ile Asn Leu Gln Pro Glu Val Gln Val Asp Thr Ser Glu
2945                 2950                2955

Val Gly Ile Thr Ile Ile Gly Lys Glu Ala Val Met Thr Thr Gly
2960                 2965                2970

Val Thr Pro Val Met Glu Lys Val Glu Pro Asp Thr Asp Asn Asn

-continued

```
                2975                2980                2985
Gln Ser Ser Val Lys Ile Gly Leu Asp Glu Gly Asn Tyr Pro Gly
        2990                2995                3000
Pro Gly Val Gln Thr His Thr Leu Val Glu Glu Ile His Asn Lys
        3005                3010                3015
Asp Ala Arg Pro Phe Ile Met Val Leu Gly Ser Lys Ser Ser Met
        3020                3025                3030
Ser Asn Arg Ala Lys Thr Ala Arg Asn Ile Asn Leu Tyr Thr Gly
        3035                3040                3045
Asn Asp Pro Arg Glu Ile Arg Asp Leu Met Ala Glu Gly Arg Ile
        3050                3055                3060
Leu Val Val Ala Leu Arg Asp Ile Asp Pro Asp Leu Ser Glu Leu
        3065                3070                3075
Val Asp Phe Lys Gly Thr Phe Leu Asp Arg Glu Ala Leu Glu Ala
        3080                3085                3090
Leu Ser Leu Gly Gln Pro Lys Pro Lys Gln Val Thr Lys Ala Ala
        3095                3100                3105
Ile Arg Asp Leu Leu Lys Glu Glu Arg Gln Val Glu Ile Pro Asp
        3110                3115                3120
Trp Phe Thr Ser Asp Asp Pro Val Phe Leu Asp Ile Ala Met Lys
        3125                3130                3135
Lys Asp Lys Tyr His Leu Ile Gly Asp Val Val Glu Val Lys Asp
        3140                3145                3150
Gln Ala Lys Ala Leu Gly Ala Thr Asp Gln Thr Arg Ile Val Lys
        3155                3160                3165
Glu Val Gly Ser Arg Thr Tyr Thr Met Lys Leu Ser Ser Trp Phe
        3170                3175                3180
Leu Gln Ala Ser Ser Lys Gln Met Ser Leu Thr Pro Leu Phe Glu
        3185                3190                3195
Glu Leu Leu Arg Cys Pro Pro Ala Thr Lys Ser Asn Lys Gly
        3200                3205                3210
His Met Ala Ser Ala Tyr Gln Leu Ala Gln Gly Asn Trp Glu Pro
        3215                3220                3225
Leu Gly Cys Gly Val His Leu Gly Thr Val Pro Ala Arg Arg Val
        3230                3235                3240
Lys Met His Pro Tyr Glu Ala Tyr Leu Lys Leu Lys Asp Leu Val
        3245                3250                3255
Glu Glu Glu Glu Lys Lys Pro Arg Ile Arg Asp Thr Val Ile Arg
        3260                3265                3270
Glu His Asn Lys Trp Ile Leu Lys Lys Ile Lys Phe Gln Gly Asn
        3275                3280                3285
Leu Asn Thr Lys Lys Met Leu Asn Pro Gly Lys Leu Ser Glu Gln
        3290                3295                3300
Leu Asp Arg Glu Gly His Lys Arg Asn Ile Tyr Asn Asn Gln Ile
        3305                3310                3315
Ser Thr Val Met Ser Ser Ala Gly Ile Arg Leu Glu Lys Leu Pro
        3320                3325                3330
Ile Val Arg Ala Gln Thr Asp Thr Lys Ser Phe His Glu Ala Ile
        3335                3340                3345
Arg Asp Lys Ile Asp Lys Asn Glu Asn Arg Gln Asn Pro Glu Leu
        3350                3355                3360
His Asn Lys Leu Leu Glu Ile Phe His Thr Ile Ala Asp Pro Ser
        3365                3370                3375
```

-continued

Leu Lys His Thr Tyr Gly Glu Val Thr Trp Glu Gln Leu Glu Ala
3380                3385                3390

Gly Ile Asn Arg Lys Gly Ala Ala Gly Phe Leu Glu Lys Lys Asn
3395                3400                3405

Ile Gly Glu Val Leu Asp Ser Glu Lys His Leu Val Glu Gln Leu
3410                3415                3420

Val Arg Asp Leu Lys Ala Gly Arg Lys Ile Arg Tyr Tyr Glu Thr
3425                3430                3435

Ala Ile Pro Lys Asn Glu Lys Arg Asp Val Ser Asp Asp Trp Gln
3440                3445                3450

Ala Gly Asp Leu Val Asp Glu Lys Lys Pro Arg Val Ile Gln Tyr
3455                3460                3465

Pro Glu Ala Lys Thr Arg Leu Ala Ile Thr Lys Val Met Tyr Asn
3470                3475                3480

Trp Val Lys Gln Gln Pro Val Val Ile Pro Gly Tyr Glu Gly Lys
3485                3490                3495

Thr Pro Leu Phe Asn Ile Phe Asn Lys Val Arg Lys Glu Trp Asp
3500                3505                3510

Leu Phe Asn Glu Pro Val Ala Val Ser Phe Asp Thr Lys Ala Trp
3515                3520                3525

Asp Thr Gln Val Thr Ser Arg Asp Leu His Leu Ile Gly Glu Ile
3530                3535                3540

Gln Lys Tyr Tyr Tyr Arg Lys Glu Trp His Lys Phe Ile Asp Thr
3545                3550                3555

Ile Thr Asp His Met Val Glu Val Pro Val Ile Thr Ala Asp Gly
3560                3565                3570

Glu Val Tyr Ile Arg Asn Gly Gln Arg Gly Ser Gly Gln Pro Asp
3575                3580                3585

Thr Ser Ala Gly Asn Ser Met Leu Asn Val Leu Thr Met Ile Tyr
3590                3595                3600

Ala Phe Cys Glu Ser Thr Gly Val Pro Tyr Lys Ser Phe Asn Arg
3605                3610                3615

Val Ala Lys Ile His Val Cys Gly Asp Asp Gly Phe Leu Ile Thr
3620                3625                3630

Glu Lys Gly Leu Gly Leu Lys Phe Ser Asn Lys Gly Met Gln Ile
3635                3640                3645

Leu His Glu Ala Gly Lys Pro Gln Lys Leu Thr Glu Gly Glu Lys
3650                3655                3660

Met Lys Val Ala Tyr Lys Phe Glu Asp Ile Glu Phe Cys Ser His
3665                3670                3675

Thr Pro Val Pro Val Arg Trp Ser Asp Asn Thr Ser Ser Tyr Met
3680                3685                3690

Ala Gly Arg Asp Thr Ala Val Ile Leu Ser Lys Met Ala Thr Arg
3695                3700                3705

Leu Asp Ser Ser Gly Glu Arg Gly Thr Thr Ala Tyr Glu Lys Ala
3710                3715                3720

Val Ala Phe Ser Phe Leu Leu Met Tyr Ser Trp Asn Pro Leu Val
3725                3730                3735

Arg Arg Ile Cys Leu Leu Val Leu Ser Gln Arg Pro Glu Thr Ala
3740                3745                3750

Pro Ser Thr Gln Thr Thr Tyr Tyr Tyr Lys Gly Asp Pro Ile Gly
3755                3760                3765

-continued

```
Ala Tyr Lys Asp Val Ile Gly Arg Asn Leu Ser Glu Leu Lys Arg
    3770            3775                3780
Thr Gly Phe Glu Lys Leu Ala Asn Leu Asn Leu Ser Leu Ser Thr
    3785            3790                3795
Leu Gly Ile Trp Thr Lys His Thr Ser Lys Arg Ile Ile Gln Asp
    3800            3805                3810
Cys Val Ala Ile Gly Lys Glu Glu Gly Asn Trp Leu Val Asn Ala
    3815            3820                3825
Asp Arg Leu Ile Ser Ser Lys Thr Gly His Leu Tyr Ile Pro Asp
    3830            3835                3840
Lys Gly Phe Thr Leu Gln Gly Lys His Tyr Glu Gln Leu Gln Leu
    3845            3850                3855
Gly Ala Glu Thr Asn Pro Val Met Gly Val Gly Thr Glu Arg Tyr
    3860            3865                3870
Lys Leu Gly Pro Ile Val Asn Leu Leu Leu Arg Arg Leu Lys Val
    3875            3880                3885
Leu Leu Met Ala Ala Val Gly Ala Ser Ser
    3890            3895

<210> SEQ ID NO 7
<211> LENGTH: 19
<212> TYPE: DNA
<213> ORGANISM: Artificial Sequence
<220> FEATURE:
<223> OTHER INFORMATION: synthietic oligonucleotide primer NADL4744

<400> SEQUENCE: 7
cgtggcttct tggtacggg                                                19

<210> SEQ ID NO 8
<211> LENGTH: 22
<212> TYPE: DNA
<213> ORGANISM: Artificial Sequence
<220> FEATURE:
<223> OTHER INFORMATION: synthetic oligonucleotide primer NADL4744

<400> SEQUENCE: 8
agcggtatat tgtacaaagc ca                                            22

<210> SEQ ID NO 9
<211> LENGTH: 24
<212> TYPE: DNA
<213> ORGANISM: Artificial Sequence
<220> FEATURE:
<223> OTHER INFORMATION: synthetic oligonucleotide primer 53637U2

<400> SEQUENCE: 9
tgcacgatct gtgaagggaa agaa                                          24

<210> SEQ ID NO 10
<211> LENGTH: 24
<212> TYPE: DNA
<213> ORGANISM: Artificial Sequence
<220> FEATURE:
<223> OTHER INFORMATION: synthetic oligonucleotide primer NADL4844

<400> SEQUENCE: 10
tgcactgtat gtgagggccg agag                                          24

<210> SEQ ID NO 11
<211> LENGTH: 27
<212> TYPE: DNA
```

```
<213> ORGANISM: Pestivirus bovine viral diarrhea virus 1
<220> FEATURE:
<221> NAME/KEY: misc_feature
<223> OTHER INFORMATION: Bovine Viral Diarrhea Virus 1 strain NADL
<220> FEATURE:
<221> NAME/KEY: misc_feature
<223> OTHER INFORMATION: partial nucleotide sequence preceding the 270
      nucleotide insert for strain NADL

<400> SEQUENCE: 11
tttataaggg aaggcaactt tgagggt                                            27

<210> SEQ ID NO 12
<211> LENGTH: 9
<212> TYPE: PRT
<213> ORGANISM: Pestivirus bovine viral diarrhea virus 1
<220> FEATURE:
<221> NAME/KEY: misc_feature
<223> OTHER INFORMATION: Bovine Viral Diarrhea Virus 1 strain NADL
<220> FEATURE:
<221> NAME/KEY: misc_feature
<223> OTHER INFORMATION: partial amino acid sequence preceding the 90
      amino acid insert for strain NADL

<400> SEQUENCE: 12

Phe Ile Arg Glu Gly Asn Phe Glu Gly
1               5

<210> SEQ ID NO 13
<211> LENGTH: 36
<212> TYPE: DNA
<213> ORGANISM: Pestivirus bovine viral diarrhea virus 1
<220> FEATURE:
<221> NAME/KEY: misc_feature
<223> OTHER INFORMATION: Bovine Viral Diarrhea Virus 1 strain NADL
<220> FEATURE:
<221> NAME/KEY: misc_feature
<223> OTHER INFORMATION: Partial nucleotide sequence following the 270
      nucleotide insert for strain NADL

<400> SEQUENCE: 13
cctttcaggc aggaatacaa tggctttgta caatat                                  36

<210> SEQ ID NO 14
<211> LENGTH: 12
<212> TYPE: PRT
<213> ORGANISM: Pestivirus bovine viral diarrhea virus 1
<220> FEATURE:
<221> NAME/KEY: misc_feature
<223> OTHER INFORMATION: Bovine Viral Diarrhea Virus 1 strain NADL
<220> FEATURE:
<221> NAME/KEY: misc_feature
<223> OTHER INFORMATION: partial amino acid sequence following the 90
      amino acid insert for strain NADL

<400> SEQUENCE: 14

Pro Phe Arg Gln Glu Tyr Asn Gly Phe Val Gln Tyr
1               5                   10

<210> SEQ ID NO 15
<211> LENGTH: 18
<212> TYPE: DNA
<213> ORGANISM: Pestivirus bovine viral diarrhea virus 2
<220> FEATURE:
<221> NAME/KEY: misc_feature
<223> OTHER INFORMATION: Bovine Viral Diarrhea Virus 2 strain 53637
<220> FEATURE:
<221> NAME/KEY: misc_feature
<223> OTHER INFORMATION: partial nucleotide sequence preceding the 393
      nucleotide insert for strain 53637
```

```
<400> SEQUENCE: 15
tttataagag aaggacgc                                                 18

<210> SEQ ID NO 16
<211> LENGTH: 6
<212> TYPE: PRT
<213> ORGANISM: Pestivirus bovine viral diarrhea virus 2
<220> FEATURE:
<221> NAME/KEY: misc_feature
<223> OTHER INFORMATION: Bovine Viral Diarrhea Virus 2 strain 53637
<220> FEATURE:
<221> NAME/KEY: misc_feature
<223> OTHER INFORMATION: partial amino acid sequence preceding the 131
      amino acid insert for strain 53637

<400> SEQUENCE: 16

Phe Ile Arg Glu Gly Arg
1               5

<210> SEQ ID NO 17
<211> LENGTH: 30
<212> TYPE: DNA
<213> ORGANISM: Pestivirus bovine viral diarrhea virus 2
<220> FEATURE:
<221> NAME/KEY: misc_feature
<223> OTHER INFORMATION: Bovine Viral Diarrhea Virus 2 strain 53637
<220> FEATURE:
<221> NAME/KEY: misc_feature
<223> OTHER INFORMATION: partial nucleotide sequence following the 393
      nucleotide insert for strain 53637

<400> SEQUENCE: 17
agggaagagt ataagggtta cgtccaatac                                    30

<210> SEQ ID NO 18
<211> LENGTH: 10
<212> TYPE: PRT
<213> ORGANISM: Pestivirus bovine viral diarrhea virus 2
<220> FEATURE:
<221> NAME/KEY: misc_feature
<223> OTHER INFORMATION: ovine Viral Diarrhea Virus 2 strain 53637
<220> FEATURE:
<221> NAME/KEY: misc_feature
<223> OTHER INFORMATION: partial amino acid sequence following the 131
      amino acid insert for strain 53637

<400> SEQUENCE: 18

Arg Glu Glu Tyr Lys Gly Tyr Val Gln Tyr
1               5                   10
```